United States Patent
Montague, Jr. et al.

(10) Patent No.: US 10,634,181 B2
(45) Date of Patent: Apr. 28, 2020

(54) ASYMMETRICAL-FORCE CONNECTOR SYSTEM

(71) Applicant: Case Western Reserve University, Cleveland, OH (US)

(72) Inventors: Frederick W. Montague, Jr., Cleveland, OH (US); Brian Smith, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 628 days.

(21) Appl. No.: 15/747,265

(22) PCT Filed: Mar. 12, 2013

(86) PCT No.: PCT/US2013/030333
§ 371 (c)(1),
(2) Date: Jan. 24, 2018

(87) PCT Pub. No.: WO2014/142799
PCT Pub. Date: Sep. 18, 2014

(65) Prior Publication Data
US 2018/0233849 A1    Aug. 16, 2018

(51) Int. Cl.
*F16B 21/18* (2006.01)
*H01R 4/48* (2006.01)
(Continued)

(52) U.S. Cl.
CPC .......... *F16B 21/183* (2013.01); *A61N 1/3752* (2013.01); *H01R 4/4863* (2013.01);
(Continued)

(58) Field of Classification Search
CPC ....... A61N 1/3752; F16B 21/16; F16B 21/18; F16B 21/183; F16B 21/186; F16F 1/12;
(Continued)

(56) References Cited

U.S. PATENT DOCUMENTS 2,819,063 A    1/1958  Neidhart
3,910,566 A *  10/1975 Pedersen ............... F16B 21/078
                                                      267/167
(Continued)

FOREIGN PATENT DOCUMENTS

CN    202308438       7/2012
DE    3227431 A1 *   8/1983  ............... E05C 9/18
(Continued)

OTHER PUBLICATIONS

International Search Report and Written Opinion for corresponding PCT Application No. PCT/US2013/030333, dated Nov. 7, 2013, pp. 1-10.

*Primary Examiner* — Josh Skroupa
(74) *Attorney, Agent, or Firm* — Tarolli, Sundheim, Covell & Tummino LLP

(57) ABSTRACT

An asymmetrical-force connector system includes a socket having a longitudinally-oriented shaft bore defining a bore axis. A spring-receiving cavity is coaxial with the bore axis and extends laterally around the shaft bore. The spring-receiving cavity has an inner circumference that is open to the shaft bore. A toroidal canted coil spring is located at least partially within the spring-receiving cavity. The toroidal canted coil spring has an inner spring circumference. A connector pin including a maximum shaft circumference is configured for selective sliding insertion into the shaft bore longitudinally from the front housing face. A v-groove extends laterally inward from the maximum shaft circumference toward the pin axis and defines a minimum shaft circumference. The connector pin is located in a maintenance position within the shaft bore when at least a portion of the toroidal canted coil spring laterally extends into the v-groove beyond the maximum shaft circumference.

13 Claims, 10 Drawing Sheets

(51) Int. Cl.
    *H01R 13/187*     (2006.01)
    *H01R 13/52*      (2006.01)
    *A61N 1/375*      (2006.01)
    *A61N 1/37*       (2006.01)

(52) U.S. Cl.
    CPC ....... *H01R 13/187* (2013.01); *H01R 13/5219* (2013.01); *H01R 2201/12* (2013.01); *Y10T 403/581* (2015.01)

(58) Field of Classification Search
    CPC .... H01R 4/4863; H01R 13/05; H01R 13/187; H01R 13/193; H01R 13/2421; H01R 13/514; H01R 13/5219; Y10T 403/4637; Y10T 403/581; Y10T 403/60; Y10T 403/602; Y10T 403/604; Y10T 403/7073
    USPC .............. 403/243, 316, 326, 327, 328, 375, 403/DIG. 14
    See application file for complete search history.

(56) References Cited

U.S. PATENT DOCUMENTS

| | | | |
|---|---|---|---|
| 4,805,943 A * | 2/1989 | Balsells | ................ F16B 21/078 |
| | | | 267/167 |
| 4,893,795 A | 1/1990 | Balsells | |
| 4,907,788 A | 3/1990 | Balsells | |
| 5,082,390 A * | 1/1992 | Balsells | .................. F16B 21/18 |
| | | | 285/318 |
| 5,769,671 A | 6/1998 | Lim | |
| 6,835,084 B2 | 12/2004 | Poon et al. | |
| 7,260,436 B2 | 8/2007 | Kilgore et al. | |
| 8,057,270 B2 * | 11/2011 | Shimazu | ............... H01R 13/187 |
| | | | 439/827 |
| 8,166,623 B2 * | 5/2012 | Balsells | ................. F16L 37/084 |
| 8,167,285 B2 * | 5/2012 | Balsells | .................. F16B 21/18 |
| | | | 267/1.5 |
| 8,382,532 B2 * | 2/2013 | Sjostedt | ............... H01R 13/187 |
| | | | 439/817 |
| 9,267,526 B2 * | 2/2016 | Balsells | .................. F16B 21/18 |
| 9,293,849 B2 * | 3/2016 | Balsells | ................. H01R 13/03 |
| 9,482,255 B2 * | 11/2016 | Changsrivong | .......... F16B 17/00 |
| 9,677,587 B2 * | 6/2017 | Changsrivong | .......... F16B 17/00 |
| 9,829,028 B2 * | 11/2017 | Changsrivong | ....... F16B 21/073 |
| 9,950,180 B2 * | 4/2018 | Janzig | ............... A61N 1/3752 |
| 2006/0083582 A1 | 4/2006 | Balsells | |
| 2006/0127170 A1 | 6/2006 | Balsells | |
| 2011/0121850 A1 | 5/2011 | Lee | |
| 2011/0266120 A1 * | 11/2011 | Nakauchi | ................ H01H 1/385 |
| | | | 200/252 |
| 2012/0301248 A1 | 11/2012 | Arnold et al. | |

FOREIGN PATENT DOCUMENTS

| | | | |
|---|---|---|---|
| EP | 0649994 A1 * | 4/1995 | ................ F16B 9/02 |
| WO | 88/10358 A1 | 12/1988 | |

* cited by examiner

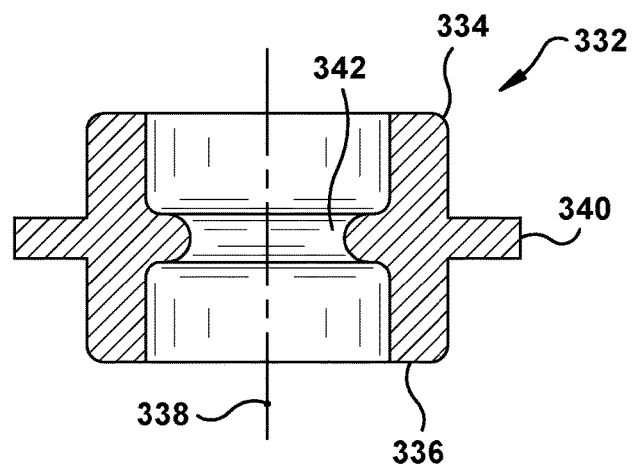
Fig. 3
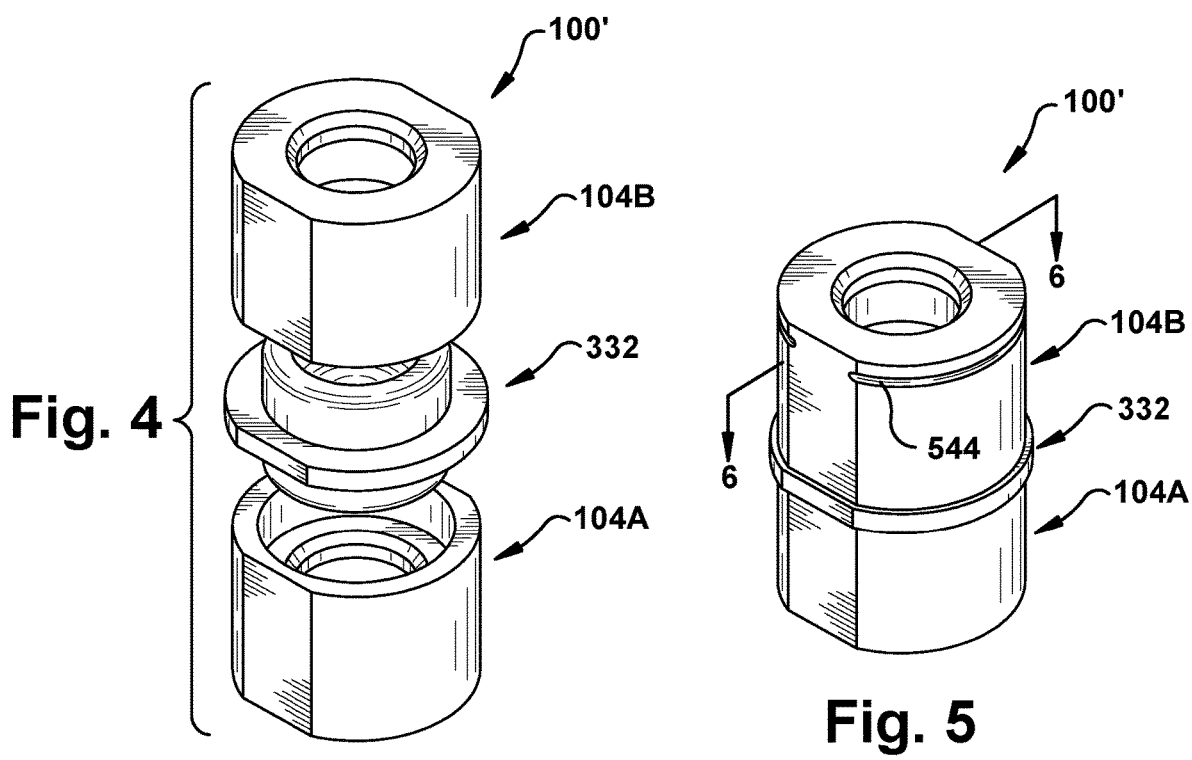
Fig. 4
Fig. 5

ASYMMETRICAL-FORCE CONNECTOR SYSTEM

TECHNICAL FIELD

The present invention relates to an apparatus and method for use of an asymmetrical-force connector system and, more particularly, to an asymmetrical-force connector system for use in a medical device.

BACKGROUND OF THE INVENTION

In the medical field, it is becoming increasingly common for small electrical devices to be implanted into a patient's body and dwell within to provide some therapeutic effect on an ongoing basis. For example, implanted neuroprosthetic devices may include a stimulating electrode, a computing or instruction-providing block connected to the electrode, and a power source (e.g., a battery) connected to the computing block and/or the electrode.

In some use environments, the electrode, computing block, and/or power source may be located some distance from each other because of, for example, space constraints in the area of the body being treated. Accordingly, medical providers often will provide these components in a modular format, with connecting wires of any desired length(s) linking the components into a complete system. In this manner, the components can each be located within the patient's body as desired, relatively unconstrained by available space at/near the therapeutic site.

During implantation surgery for a modular device, the surgeon places each component (electrode, computing block, power source, wire(s)) of the device into its desired position and, shortly before or after the placement, connects the components together by plugging a male connecting tip on one component into a female connecting socket on another component. This modular construction, having reversible connections, allows for custom-combined groups of components to be used for a particular patient (e.g., customized connecting wire lengths) as well as leaving open the potential of easy maintenance, upgrades, and/or replacement of components as opposed to a hard-wired, non-modular device.

Due to saline, blood, or other operating-room fluids and/or patient tissues, the components are often rather slippery and may be difficult to grasp firmly due to these extra substances and/or the position/location of the component within the body. Therefore, the surgeon wants the plug-in portion of the operation (insertion of the male connecting tip into the female connecting socket) to occur reliably with relatively low insertion force, to avoid damaging nearby body tissues or other components of the device.

However, a certain amount of retention force is needed to insure that the connection has been made firmly enough to resist inadvertent post-operative pull-out or retraction forces, such as those generated on the body tissues surrounding the components by normal movement of the patient. Accordingly, it can be difficult to balance the concurrent desires for relatively small insertion forces and relatively large retraction forces in connected-component medical devices. Currently, set screws are used to help maintain the connection. However, in the operative environment, the small size of the set screws and "envelope" of space needed to manipulate the installation tools adds unwanted complexity and inconvenience to an already difficult task.

SUMMARY OF THE INVENTION

In an embodiment of the present invention, an asymmetrical-force connector system is described. A socket includes a housing shell, having oppositely disposed front and rear housing faces and a longitudinally-oriented shaft bore extending longitudinally through the housing shell and linking the front and rear housing faces. The shaft bore defines a bore axis. A spring-receiving cavity is coaxial with the bore axis and extends laterally around an entirety of the shaft bore. The spring-receiving cavity has an inner circumference that is open to the shaft bore. A toroidal canted coil spring is located at least partially within the spring-receiving cavity. The toroidal canted coil spring has a laterally-oriented inner spring circumference coaxial with the bore axis and extending laterally around an entirety of the shaft bore. A connector pin is configured for selective sliding insertion into the shaft bore longitudinally from the front housing face. The connector pin includes an elongate shaft having proximal and distal shaft ends and defining a pin axis. The shaft has a laterally-oriented maximum circumference that is larger than the inner spring circumference. A v-groove extends laterally inward from the maximum shaft circumference toward the pin axis. The v-groove is located longitudinally between the proximal and distal shaft ends and extends circumferentially around the entirety of the shaft to define a minimum shaft circumference as the apex of an included angle, as viewed perpendicular to the pin axis. The v-groove has a proximal groove face extending laterally and proximally outward from the minimum shaft circumference of the shaft at an acute angle with respect to the pin axis and a distal groove face extending laterally and distally outward from the minimum shaft circumference of the shaft at an obtuse angle with respect to the pin axis. The connector pin is located in a maintenance position within the shaft bore when at least a portion of the connector pin is located longitudinally between the front and rear housing faces with at least a portion of the toroidal canted coil spring laterally extending into the v-groove beyond the maximum shaft circumference.

In an embodiment of the present invention, a method of use of an asymmetrical-force connector system is described. A socket is provided. The socket includes a longitudinally-oriented shaft bore extending thereinto to define a longitudinal bore axis. The socket includes a toroidal canted coil spring having an inner spring circumference extending laterally around the shaft bore. An elongate connector pin having a longitudinally asymmetrical v-groove extending laterally around a circumference of the connector pin is provided. At least a portion of the connector pin is inserted longitudinally into the shaft bore. At least a portion of the connector pin is passed through the inner spring circumference in a longitudinally-oriented insertion direction. The toroidal canted coil spring is compressed laterally outward from the bore axis by exertion of an insertion force against the toroidal canted coil spring with the portion of the connector pin passing therethrough. The toroidal canted coil spring is allowed to at least partially rebound from the insertion force by aligning the toroidal canted coil spring and the v-groove in the same longitudinal location relative to each other, such that at least a portion of the toroidal canted coil spring laterally enters the v-groove and a maintenance force develops laterally between the toroidal canted coil spring and the connector pin at the v-groove. The maintenance force is overcome with a retraction force to pass at least a portion of the connector pin through the inner spring circumference in a longitudinally-oriented retraction direction, longitudinally opposite the insertion direction. The toroidal canted coil spring is compressed laterally outward from the bore axis by exerting the retraction force against the toroidal canted coil spring with the portion of the connector pin passing therethrough. The connector pin is removed from the socket. The retraction force, to overcome the maintenance force and allow the connector pin to move in the retraction direction, is substantially greater than the insertion force to move the connector pin in the insertion direction due to the relative designs of the v-groove and the toroidal canted coil spring.

BRIEF DESCRIPTION OF THE DRAWINGS

For a better understanding of the invention, reference may be made to the accompanying drawings, in which:

FIG. 3 is a cross-sectional side view of a component of the present invention;

FIG. 4 is an exploded perspective view of a component of the present invention;

FIG. 5 is an assembled perspective view of the component of FIG. 4;

DESCRIPTION OF EMBODIMENTS

Figure 1:
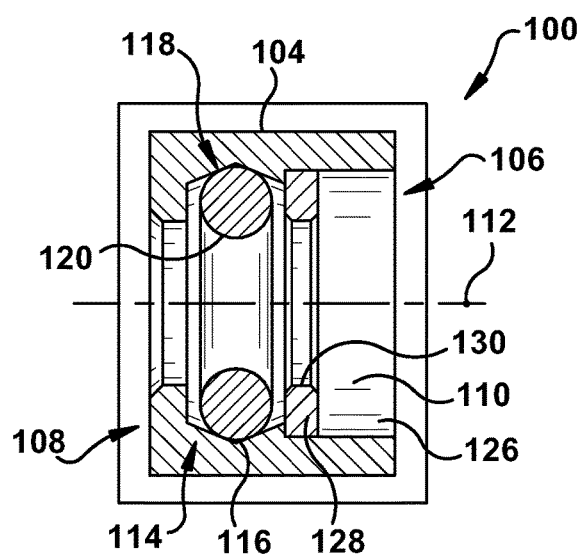
FIG. 1 is a cross-sectional side view of a prior art device.

FIG. 1 depicts a cross-sectional view of a prior art socket 100 which can be used with an asymmetrical-force connector system 102 according to the present invention. The socket 100 includes a housing shell 104 including oppositely disposed front and rear housing faces 106 and 108, respectively. In the orientation of FIG. 1, the front housing face 106 is toward the right side of the page and the rear housing face 108 is toward the left side of the page. However, one of ordinary skill in the art will understand that the directional conventions used herein for ease of description are not absolute, and that "front" and "rear" could be differently defined/used for various use environments of the present invention.

A longitudinally-oriented shaft bore 110 extends longitudinally through the housing shell 104 and links the front and rear housing faces 106 and 108. The shaft bore 110 defines a bore axis 112, which is collinear with a longitudinal axis of the depicted socket 100.

The socket 100 also includes a spring-receiving cavity 114 which is coaxial with the bore axis 112 and extends laterally around an entirety of the shaft bore 110. The term "lateral" herein is used to indicate a direction that is perpendicular to the bore/longitudinal axis 112—i.e., a "lateral" direction extends into and out of the plane of the page in FIG. 1. The spring-receiving cavity 114 includes an inner circumference 116 that is open to the shaft bore 110. As shown in FIG. 1, the inner circumference 116 is located at an apex of the v-shaped cross-section of the spring-receiving cavity 114, for reasons which will be discussed below. However, the inner circumference 116 could be defined elsewhere on a spring-receiving cavity, particularly one having a cross-section that is not v-shaped. Optionally, a plurality of spring-receiving cavities 114 may be provided to a single socket 100, with each of the spring-receiving cavities being longitudinally spaced from one another along the shaft bore 110.

A toroidal canted coil spring 118 may be located at least partially within the spring-receiving cavity 114. The toroidal canted coil spring 118 may have a laterally-oriented inner spring circumference 120 that is coaxial with the bore axis 112 and extends laterally around an entirety of the shaft bore 110. The toroidal canted coil spring 118 may be, for example, similar to that shown in U.S. Pat. No. 4,893,795, issued 16 Jan. 1990 to Peter J. Balsells. A socket 100, such as an example type which may be suitable for use with the present invention, is commercially available as the Bal Conn product line from Bal Seal Engineering, Inc. of Foothill Ranch, Calif.

Figure 2A:
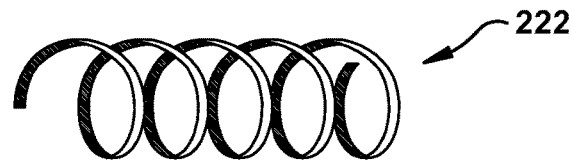
FIGS. 2A-2D illustrate various example configurations for a component of the prior art device of FIG. 1.
Figure 2B:
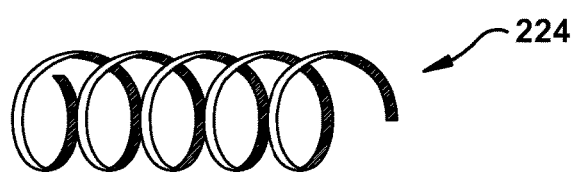
Figure 2C:
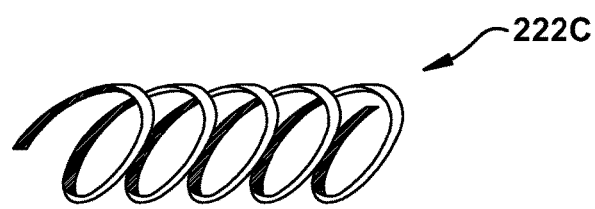
Figure 2D:
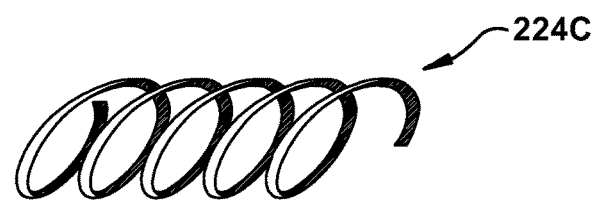

The construction and orientation of the toroidal canted coil spring 118, and related physical responses/properties of the socket 100, may be of interest in particular use environments of the present invention. FIGS. 2A-2D schematically depict various physical properties of example springs known in the art. Springs may be wound in either a right-hand or left-hand direction, and may also be canted, or skewed, in either direction. FIG. 2A depicts an uncanted right-hand wound spring 222. FIG. 2B depicts an uncanted left-hand wound spring 224. FIG. 2C depicts a canted right-hand wound spring 222C. FIG. 2D depicts a canted left-hand wound spring 224C. The handedness of the spring windings is defined similarly to the way that right-hand or left-hand screw threads are defined.

To create a toroidal canted coil spring 118, the two ends of a straight/linear canted spring 222C or 224C are connected together to form the donut- or circular-shaped toroidal canted coil spring 118. Toroidal canted coil springs 118 can be inserted into the spring receiving cavity 114 in a clockwise or counterclockwise orientation and may be made from right-hand or left-hand wound springs. Accordingly, four different types of toroidal canted coil springs are available for use in the present invention:

(1) clockwise-canted, right-hand wound
(2) clockwise-canted, left-hand wound
(3) counterclockwise-canted, right-hand wound
(4) counterclockwise-canted, left-hand wound It should be noted that that the spring of configuration #3 above is substantially the same spring as in configuration #1 except that the spring of configuration #3 is "upside down" as compared to that of #1. Similarly, the spring of configuration #4 is an inverted version of the spring of configuration #2. Because the apparent orientation and winding/canting directions of the springs are dependent upon the point of view of the observer (analogous to the hands of a clock seeming to move counterclockwise if viewed from a rear surface of the clock face), one of ordinary skill in the art will understand that the "upside down" characterizations above are, similarly, relative to the observer's position. Stated differently, if a clockwise-canted toroidal spring is viewed along the axis 112 in a first direction, that same spring would be identified as a counterclockwise-canted spring when viewed along axis 112 in a second direction that is opposite to the first direction. However, the spring configurations #1 through #4 can be used with the present invention as described herein, regardless of the perspective of the observer.

Each of these configurations of toroidal canted coil springs 118 may have different effects upon the socket 100 and other components of the asymmetrical-force connector system 102 described herein, due to the differing resistances and other physical responses of the four types of toroidal canted coil springs to applied forces. One of ordinary skill in the art will be able to select, optionally with the aid of experimentation, the type of toroidal canted coil spring 118 and other spring variables (material, processing [e.g., heat-treatment], dimensions, and the like) which result in a spring of the desired physical properties in a particular use environment of the present invention.

With reference back to FIG. 1, a laterally-oriented counterbore 126 may be provided. The counterbore 126 shown here is longitudinally interposed between the spring-receiving cavity 114 and the front housing face 106, but may be located in any desired position with respect to other structures of the housing shell 104, such as longitudinally interposed between the spring-receiving cavity 114 and the rear housing face 108. Optionally, at least one washer 128 may be located in the counterbore 126. When present, the washer 128 may have a longitudinally-oriented washer bore 130 extending therethrough, the washer bore 130 laterally surrounding the shaft bore 110 and being coaxial with the bore axis 112. The washer(s) 128 may be provided for any suitable purpose. For example, when the spring-receiving cavity 114 is relatively "open" to the front and/or rear housing faces 106 and/or 108 (e.g., so that the toroidal canted coil spring 118 can be placed within the spring-receiving cavity 114 during assembly), a washer 128 may be placed/retained within an appropriately located counterbore 126 (e.g., as a later step in assembly) to prevent the toroidal canted coil spring from being able to exit the housing shell 104 by passing longitudinally out through the counterbore 126. Particularly if the washer 128 is at least partially resilient, it may also or instead serve a sealing function by pressing laterally inward toward the bore axis 112 against a structure (not shown in FIG. 1) which is being inserted into the shaft bore 110.

Figure 6:
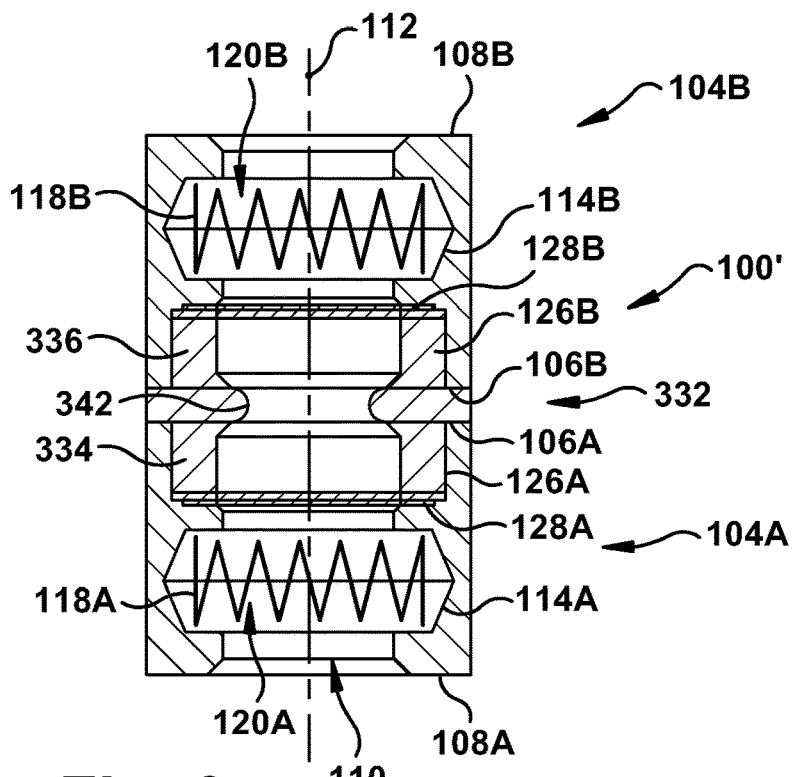
FIG. 6 is a cross-sectional view taken along line 6-6 of FIG. 5.

With reference now to FIG. 3, an intermediate member 332 may be provided to assist with formation of a multi-shell socket 100', shown in FIGS. 4-6. When present, the intermediate member 332 may include oppositely facing front and rear protrusions 334 and 336, located longitudinally apart from one another along a seal axis 338, along with a sealing disc 340 located longitudinally interposed between the front and rear protrusions.

Optionally, the socket 100' may include multiple housing shells 104 and their related components (toroidal canted coil springs 118, washers 128, or any other components), as shown in exploded view in FIG. 4, in assembled perspective view in FIG. 5, and in cross-sectional view in FIG. 6. In the multi-shell socket 100' shown in the Figures, first and second housing shells 104A and 104B are shown. However, any suitable number of housing shells 104, oriented in any suitable direction(s) relative to one another, may be included in a socket 100 without harm to the present invention, optionally with appropriately designed intermediate members 332 interposed longitudinally between any or all adjacent housing shells to achieve a desired effect.

The intermediate member 332 may be longitudinally interposed between the first and second housing shells 104A and 104B, as shown in FIGS. 4-6. In this description, it is presumed that the first and second housing shells 104A and 104B are substantially the same, other than as noted in the below description. However, one of ordinary skill in the art could provide differently configured housing shells 104 collectively forming a socket 100 for a particular use environment of the present invention. In the below description, and as is shown in detail in FIG. 6, the first housing shell 104A has oppositely disposed front and rear first housing faces 106A and 108A and a first shaft bore 110A. The multi-shell socket 100' includes a second housing shell 104B having oppositely disposed front and second rear housing faces 106B and 108B and a longitudinally-oriented second shaft bore 110B extending longitudinally through the second housing shell 104B and linking the front and second rear housing faces. The second shaft bore 110B is located collinearly with, and is longitudinally adjacent to, the first shaft bore 110A. A second spring-receiving cavity 114B is coaxial with the bore axis 112 and extends laterally around an entirety of the second shaft bore 110B. The second spring-receiving cavity 114B has a second inner spring circumference 120B that is open to the second shaft bore 110B. A second toroidal canted coil spring 118B is located at least partially within the second spring-receiving cavity 114B, the second toroidal canted coil spring having a laterally-oriented second inner spring circumference 120B coaxial with the bore axis 112 and extending laterally around an entirety of the second shaft bore 110B.

As described herein, the first and second housing shells 104A and 104B are oriented in opposite longitudinal directions, as seen in FIG. 6. That is, the second front housing face 106B is located longitudinally interposed between the rear first housing face 108A and the second rear housing face 108B. Stated differently, the first and second housing shells 104A and 104B are in "mirror image" orientations relative to each other across the intermediate member 332. This may be helpful, for example, if the washers 128A and 128B are cooperatively acting to seal the toroidal canted coil springs 118A and 118B from each other. As another example of a situation in which the first and second housing shells 104A and 104B may be desired to be oriented in opposite longitudinal directions as shown, the properties of the particular types (handedness and cant direction) of toroidal canted coil springs 118A and 118B present may be different depending upon the longitudinal direction along which force is applied, and reversing these toroidal canted coil springs relative to each other may provide some desired force exertion characteristics to the socket 100'.

In order to connect the first and second housing shells 104A and 104B together into the arrangement shown in FIGS. 5-6, both the front and rear protrusions 334 and 336 should be configured for insertion into corresponding structures of the first and second housing shells 104A and 104B. For example, and as shown in the cross-sectional view of FIG. 6, the front protrusion 334 could be inserted in a counterbore 126A in the first front housing face 106A, while the second protrusion 336 could be inserted in a counterbore 126B in the second front housing face 106B. If these protrusion/counterbore components are sized appropriately, friction between the intermediate member 332 and the first and second front housing faces 106A and 106B may be sufficient to hold the intermediate member and first and second housing shells 104A and 104B together in a male/female mating arrangement to form a multi-shell socket 100'. Alternatively or additionally, another structure or substance such as, but not limited to, a snap ring, a set screw, an adhesive, a weld, a housing/enclosure, or the like, may be provided to assist with maintaining the desired connections. Optionally, a resilient intermediate member 332 could provide some compressibility of the multi-shell socket 100' in the longitudinal direction, if desired.

When the intermediate member 332 is interposed longitudinally between the second front housing face 106B and the rear first housing face 106A as shown in FIGS. 4-6, the intermediate member 332 and first and second housings 104A and 104B cooperatively defining the shaft bore 110 therethrough. The intermediate member 332, when present, may be provided for any desired purpose, including, but not limited to, providing connection of the first and second housing shells 104A and 104B to one another; providing electrical, mechanical, or any other type of insulation to (i.e., resistance to flow between) the bodies of the first and second housing shells; and/or providing sealing to an inserted structure in a similar manner to that of the aforementioned washer(s) 128.

The sealing disc 340 may have a laterally-oriented inner intermediate circumference 342, as shown in FIG. 3, that is longitudinally coaxial (i.e., located longitudinally spaced along the same bore axis 112) with both of the first and second inner spring circumferences 120A and 120B. When present, the inner intermediate circumference 342 may be laterally smaller than both of the first and second inner spring circumferences 120A and 120B. Particularly if the intermediate member 332 is at least partially made of a resilient material, the intermediate member may provide a sealing function longitudinally between the first and second toroidal canted coil springs 118A and 118B and laterally against any structure located at least partially within the shaft bore 110 and at least partially laterally surrounded by the first and second housing shells 104A and 104B and/or any components thereof, as described below.

Incidentally, the uppermost housing shell 104B, in the orientation of FIG. 5, includes a groove 544 which may assist with identification/positioning by providing the user with a directional reference, or may be provided, in any desired location and having any desired configuration, to the socket 100 for any reason, such as to help the socket 100 engage with an installation tool (not shown) and/or engage with nearby structures, for example, when the socket forms a part of an asymmetrical-force connector system. This groove 544, which may be present on any structure of the socket 100, will not be further discussed herein.

Figure 7:
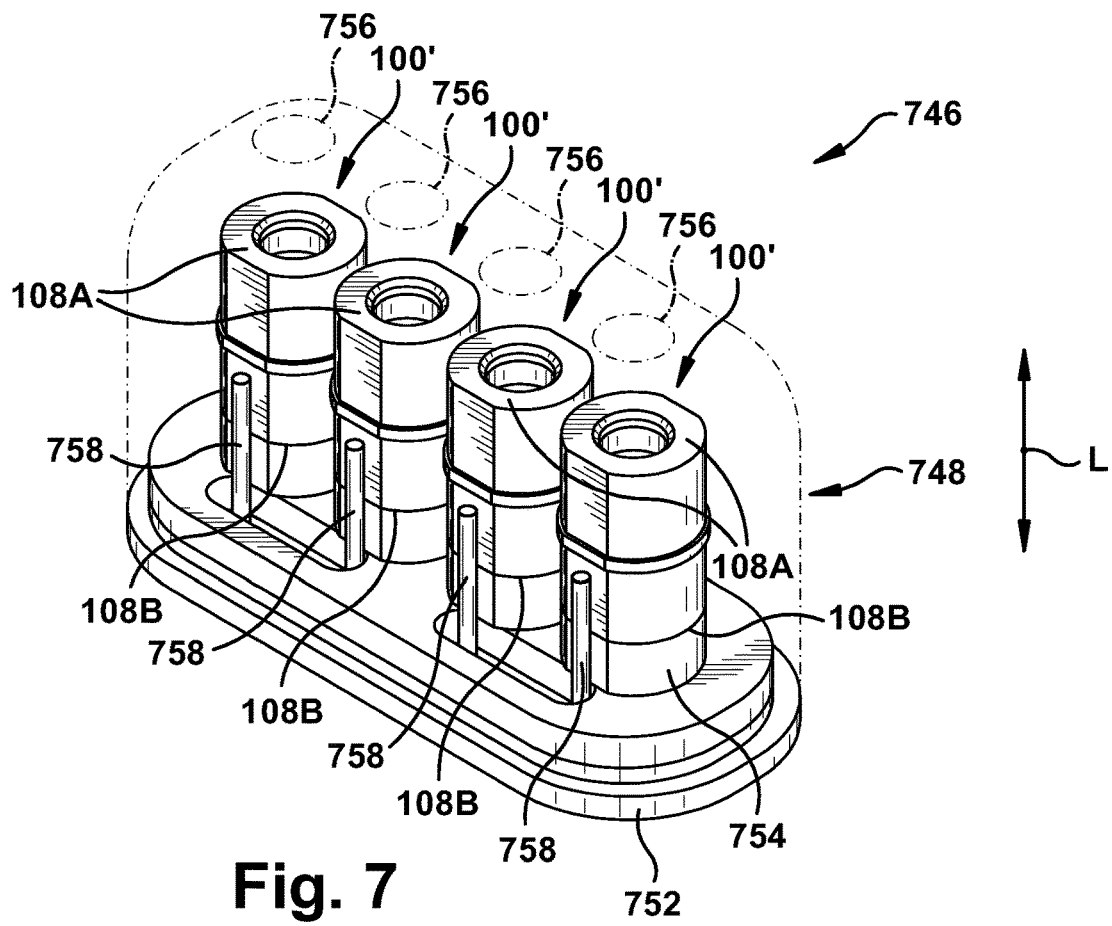
FIG. 7 is a perspective view of an optional use environment for the component of FIG. 5.

FIG. 7 depicts a portion of an optional use environment for the present invention. In FIG. 7, an interconnect device 746 includes a socket manifold 748. Here, the term "manifold" is used to reference a device or structure which includes a plurality of multi-shell sockets 100', each of which is held substantially stationary relative to one another and each of which has a shaft bore 110 exposed to the ambient environment and available to help form an electrical connection. The multi-shell sockets 100' of the socket manifold 748 shown in FIG. 7 are substantially identical to one another and are similar to the multi-shell socket 100' of FIGS. 4-6, but it is contemplated that a variety of different types of sockets—multi-shell or otherwise—could be provided by one of ordinary skill in the art for a particular use application of the present invention.

The socket manifold 748 shown in FIG. 7 includes a manifold housing 750 (shown as translucent in FIG. 7) laterally enclosing the plurality of multi-shell sockets 100'. A manifold cap 752 engages with the manifold housing 750 to "cap" the manifold housing and enclose the multi-shell sockets 100' within the body of the socket manifold 748. The manifold cap 752 includes at least one socket interface 754, which usually will be equal in number to the number of sockets 100' in the socket manifold 748. Each socket interface 754 holds a corresponding multi-shell socket 100' substantially in position within the socket manifold 748—for example a protrusion (not shown) could extend longitudinally (i.e., substantially parallel to arrow "L" in FIG. 7) into the shaft bore 110 from the second rear housing face 108B of the multi-shell sockets. This protrusion could be held therein using any desired means (e.g., adhesion, friction, mechanical [set screw, snap-fit, etc.] or the like) to prevent the multi-shell socket 100' from shifting within the manifold housing.

A plurality of manifold apertures 756—one per socket 100', in most use environments of the present invention—are each longitudinally aligned with a shaft bore 110 from a "leading" end (here, first rear housing faces 108A) of the multi-shell sockets 100'. The manifold apertures 756 place the shaft bores 110 of their respective multi-shell sockets 100' into fluid communication with an ambient atmosphere. It is contemplated that, for most use environments of the present invention, the manifold apertures 756 will have a cross-sectional (i.e., perpendicular to longitudinal direction L) shape and size commensurate with those of the shaft bore 110 at the "leading" end (here, first rear housing faces 108A) of the respective multi-shell sockets 100'. The manifold apertures 756 could, instead, differ from the cross-sectional shape and/or size of the shaft bores 110 at the interface therebetween, for any desired reason.

To form the socket manifold 748, the manifold housing 750 and manifold cap 752 could be provided separately and then assembled with the sockets 100 located within the enclosure cooperatively provided by the manifold housing and cap. Alternatively, at least a portion of the socket manifold 748 could be molded around the sockets 100—for example, the sockets could be sub-assembled to a freestanding manifold cap 752 and the resulting sub-assembly potted or otherwise molded into a substantially solid manifold housing 750 that directly contacts and surrounds the sockets.

Figure 8:
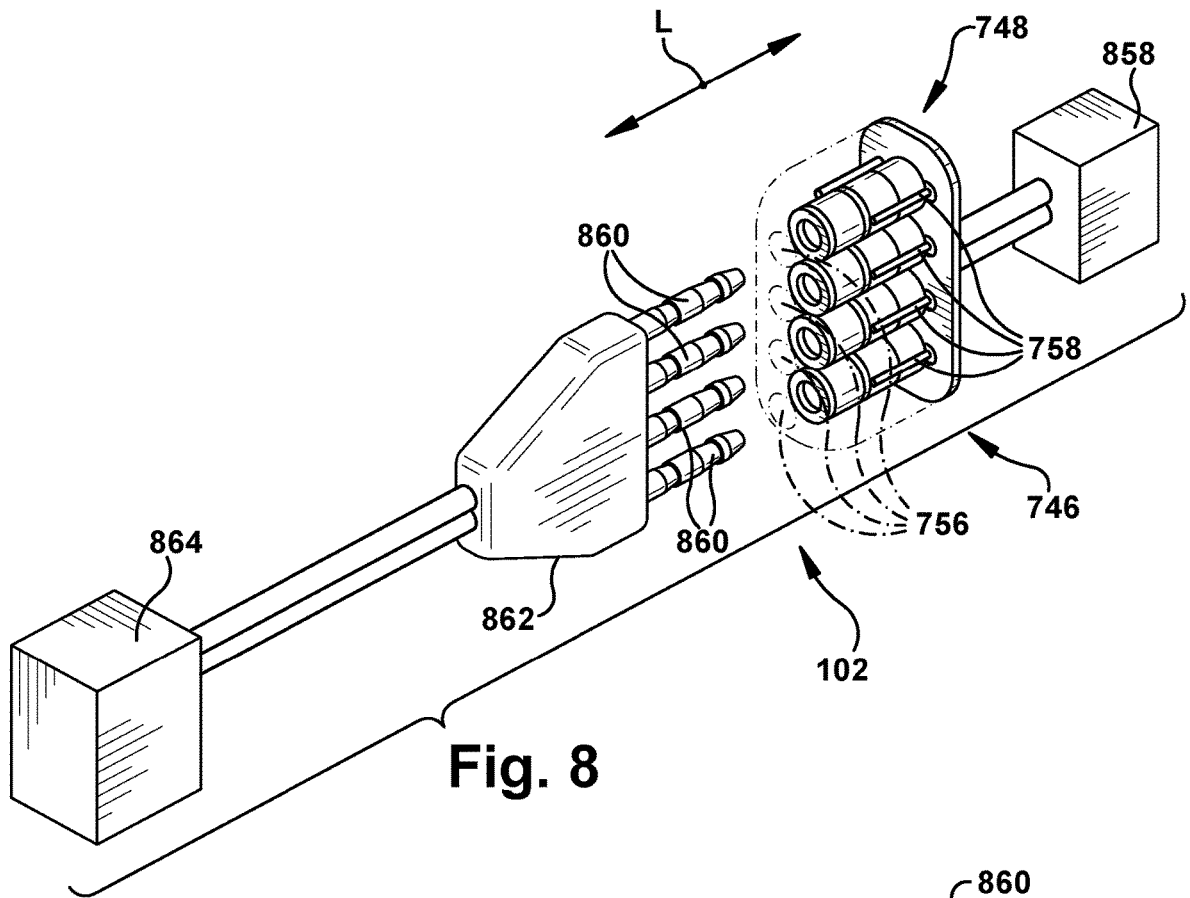
FIG. 8 is an exploded perspective view of an embodiment of the present invention, including the component of FIG. 4.

Turning to FIG. 8, an exploded view of the interconnect device 746 is shown schematically, though the socket manifold 748 (already shown in detail in FIG. 7) is left largely unnumbered, for clarity. At least one multi-shell socket 100' is in electrical contact with a first component 858, via the socket manifold 748 or portions thereof. A plurality of connector pins 860 are in electrical contact, via a pin header 862, with a second component 864. The first and second components 858 and 864 may be of any type between which an electrical connection is desired to be made, such that the asymmetrical force connector system 102 is configured to pass electrical signals to and/or from the first component 858 and the second component 864, via the interface between the socket 100 and the connector pin 860. For most use environments of the present invention, there will be at least as many sockets 100 in the socket manifold 748 as there are connector pins 860 in the pin header 862, with either a 1:1 correspondence in number and relative spacing/location/orientation between connector pins and sockets, or optionally instead a few "extra" sockets that do not have a corresponding connector pin. There could be fewer sockets 100 than connector pins 860 if, for example, "dummy pins" were used as locators or to "key" or otherwise align/orient a particular connector for a particular application.

Each connector pin 860 is inserted into its corresponding socket 100 (here, multi-shell sockets 100') via relative movement of those structures in a substantially longitudinal direction to place the first and second components 858 and 864 into electrical contact with each other via an electrically-connective interface formed between the sockets and their respective connector pins, as will be described below with reference to a single connector pin 860 and corresponding multi-shell socket 100'. One of ordinary skill in the art will be able to provide an interconnect device 746 having any suitable number of sockets 100, any suitable number of connector pins 860 (whether or not there are the same number of sockets and connector pins), and any desired physical arrangement of the connector pins on the pin header 862 and the sockets on the socket manifold 748, for a desired use environment of the present invention. For example, and as shown by communication wires 758 in FIGS. 7 and 8, the interconnect device 746 could include any suitable number, type, and configuration of interconnect wires 758 to place the connector pins 860 into electrical, mechanical, or any other desired type of connection or communication with a first component 858 in any suitable manner. Though FIG. 8 shows all of the multi-shell sockets 100' on a single socket manifold 748 and all of the connector pins 860 on a single pin header 862, it is contemplated that multiple socket manifolds and/or pin headers, each of which would carry any desired number and type of sockets 100 or connector pins, respectively, could be used as/at a single interconnect device 746 site—for example, connector pins could be each electrically connected to a different component (third, fourth, and so on), with no common structure linking all of the connector pins together into the interconnect device.

Figure 9:
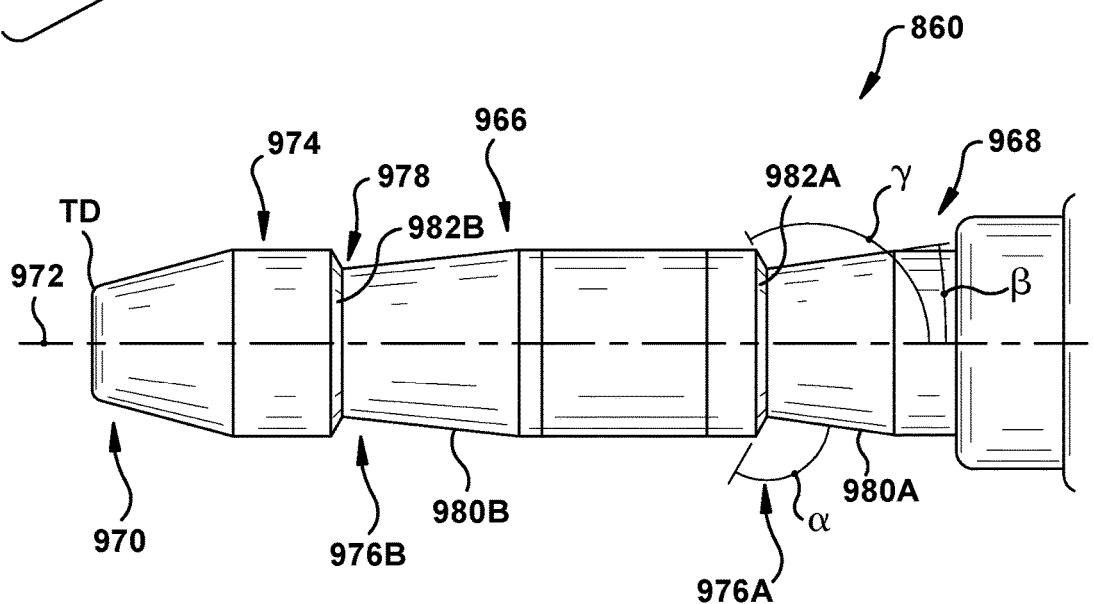
FIG. 9 is a partial side view of a component of the embodiment of FIG. 8.

FIG. 9 is a side view of a single connector pin 860 of an asymmetrical-force connector system 102. The connector pin 860 an elongate shaft 966 having proximal and distal shaft ends 968 and 970, respectively, and defining a pin axis 972. The shaft 966 has a laterally-oriented maximum shaft circumference 974 that is larger than the inner spring circumference 120 of the socket 100. A v-groove 976 extends laterally inward from the maximum shaft circumference 974 toward the pin axis 972. The v-groove 976 is located longitudinally between the proximal and distal shaft ends 968 and 970 and extends circumferentially around at least a portion of, and optionally the entirety of, the shaft to define a minimum shaft circumference 978 as the apex of an included angle α, as viewed perpendicular to the pin axis— that is, when the included angle α is viewed from a lateral direction as in FIG. 9. The included angle α may be in the range of 0-180 degrees.

The v-groove 976 is shown in the embodiment of the Figs. as having an angular, "pointed" apex at the intersection of proximal and distal groove faces 980 and 982 (e.g., the smallest-diameter portion along the pin shaft 966, as shown in FIG. 9). Although, for ease of description, the v-groove 976 is shown and discussed as having this abrupt transition, it is also contemplated that the apex of the "v" groove may, for some embodiments of the present invention, have a more gradual, radiused transition between the proximal and distal groove faces 980 and 982. In other words, the apex of the v-groove may be rounded in some embodiments, rather than the angular apex shown, for any desired reason, including, but not limited to, allowing for wider mechanical tolerances to ease manufacturing precision, avoiding a stress concentrator point, and affecting a mating function of the v-groove with another structure of the device. The below description is agnostic and apathetic as to the radiused/angular nature of the apex. Instead, the depicted embodiment is described herein with reference to the proximal and distal groove faces 980 and 982. For this embodiment, it is merely contemplated that the apex is either angular (as shown) or has a rounded radius that is smaller than the corresponding radius of the canted coil spring 118 to facilitate the described interactions between these components.

Optionally, the distal shaft end 970 may have a terminal diameter TD (i.e. the diameter of the distal face of the shaft 966), that is smaller than the maximum shaft circumference 974. When this is the case, the distal shaft end 970 may "taper down" as shown in FIG. 9, or even to a relatively sharp point (e.g., an extremely small value for TD), to help locate and center the connector pin 860 with respect to the shaft bore 110 of a socket 100. It is contemplated that the proximal shaft end 968 may be in electrical communication with a component (e.g., first or second component 858 or 864) of an apparatus such as an implanted electrical medical device (not shown).

In FIG. 9, there are two v-grooves 976A and 976B, spaced longitudinally apart along the pin axis 972 and located between the proximal and distal shaft ends 968 and 970. As both of the v-grooves 976A and 976B shown in FIG. 9 are substantially identical, for the purposes of this description, they will be referenced interchangeably herein as "v-groove 976", with the description being common to both, except when some distinction is being drawn between the proximal-most v-groove 976A and the distal-most v-groove 976B. For clarity, each of the v-grooves 976 shown in the Figures include element numbers and callout lines which are not repeated for both v-grooves, but which should be presumed to reference corresponding structures in both v-grooves unless otherwise stated.

The v-groove 976 has a proximal groove face 980 extending laterally and proximally outward from the minimum shaft circumference 978 of the shaft 966 at an acute angle β to the pin axis 972 and a distal groove face 982 extending laterally and distally outward from the minimum shaft circumference of the shaft at an obtuse angle γ. The acute and obtuse angles β and γ may be chosen by one of ordinary skill in the art, using the teachings of the present invention, to provoke desired force responses in the toroidal canted coil spring(s) 118 of the socket 100, as described below. Some example values that might be used for acute angle β are in the range of 0-90 degrees, for example, 2-10 degrees, or, as a more particular example, 5 degrees. Some example values that might be used for obtuse angle γ are in the range of 90-180 degrees, for example, 100-150 degrees. Since the difference between the acute and obtuse angles β and γ is equal to the included angle α, then, an example range of suitable values for the included angle α in some embodiments of the present inventions is 90-148 degrees.

In use, the connector pin 860 is configured for selective sliding insertion longitudinally into the shaft bore 110, as will now be shown in FIGS. 10A-10I and discussed with reference to these Figures. When one housing shell 104 is provided to an asymmetrical-force connector system 102, the connector pin 860 will often be inserted longitudinally into the shaft bore 110 from the front housing face 106, as shown in the arrangement of FIG. 1. However, since a multi-shell socket 100' is shown in FIGS. 10A-10I, the "front housing face" in these Figures (i.e., the face into which the connector pin 860 is initially inserted) is actually the rear first housing face 108A. To avoid confusion, the below description will maintain the front/rear and first/second housing appellations and orientations introduced in FIGS. 6-7 and repeated in FIG. 10A, with the exception that a front socket face 1084, encompassing the rear first housing face 108A, is considered to be the "front" of the multi-shell socket 100', and a rear socket face 1086, encompassing the rear second housing face 108B, is considered to be the "rear"

of the multi-shell socket. Under this convention, and with reference to longitudinal arrow L in FIG. 10A, the connector pin 860 enters the multi-shell socket 100' by longitudinal "insertion" movement from the right to the left, in the orientation of FIGS. 10A-10I, and the connector pin exits the multi-shell socket by longitudinal "retraction" movement from the left to the right, in the orientation of FIGS. 10A-10I.

In addition, the second housing shell 104B and associated structures are similar to the first housing shell 104A and therefore, structures of the second shell that are the same as or similar to those described with reference to the first housing shell have the same reference numbers with the addition of the suffix "B"—the suffix "A" is used herein to indicate a structure of, or related to, the first housing shell in a multi-shell socket 100'. Description of common elements and operation similar to those related to the first housing shell 104A will not be repeated with respect to the second housing shell 104B.

One of ordinary skill in the art will realize that the front/rear and first/second housing appellations and static/dynamic directional indications used in the below description of the operation of the asymmetrical-force connector system 102 are somewhat arbitrary and depend heavily on the frame of reference of the observer and the number and orientations of housing shells 104 included in the socket 100 or 100'. Accordingly, a system or device including similar structures and functions to those described with reference to FIGS. 10A-10I may be described differently (e.g., front/rear faces could be thought of as being leading/trailing faces) while still, in practice, falling under the description and claims herein.

Figure 10A:
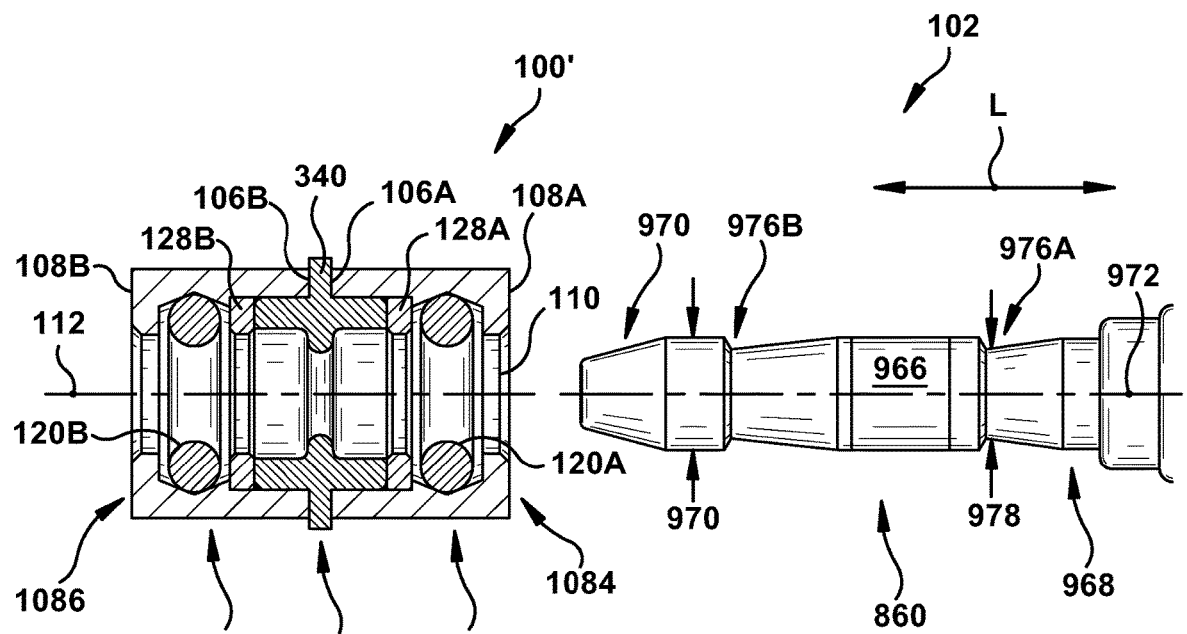
FIGS. 10A-10I schematically depict a sequence of operation of the embodiment of FIG. 8.

In order to insert the connector pin 860 into the multi-shell socket 100' via the sequence of FIGS. 10A-10I, the user longitudinally and laterally aligns these two structures, as shown in FIG. 10A, with the connector pin prepared to enter the shaft bore 110. Since the connector pin 860 and the multi-shell socket 100' remain laterally aligned throughout the depicted sequence, the pin axis 972 is presumed to be coaxial with the bore axis 112 throughout FIGS. 10A-10I.

Figure 10B:
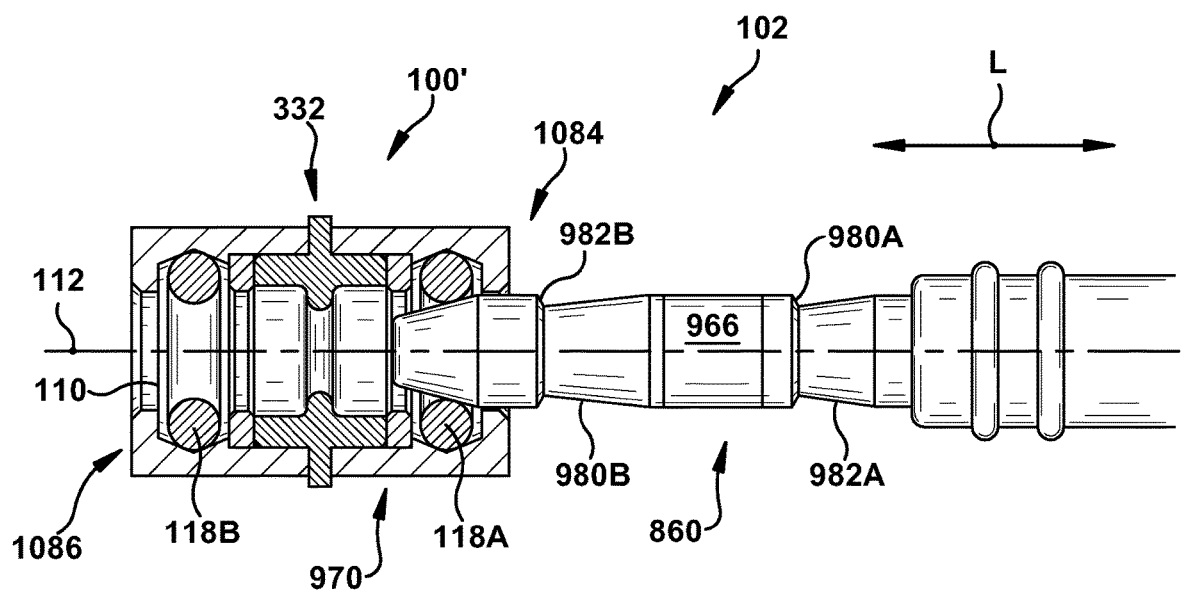

Continuing to FIG. 10B, at least a portion of the connector pin 860 (here, the distal shaft end 970) is inserted longitudinally into the shaft bore 110, optionally with centering and/or penetration assistance provided by the tapered feature near the distal shaft end of the pin shaft 966. Particularly if the inner spring circumference 120A is smaller than the maximum shaft circumference 974, the distal shaft end 970 may exert a laterally-oriented insertion force upon the first canted coil spring 118A while passing there through, to compress the first canted coil spring outward from the bore axis 112. Even if no compressive force is exerted on the first canted coil spring 118A, the connector pin 860 is subject to a longitudinally-oriented component of the insertion force that continues to slide the connector pin further into the shaft bore 110 in the insertion direction.

Figure 10C:
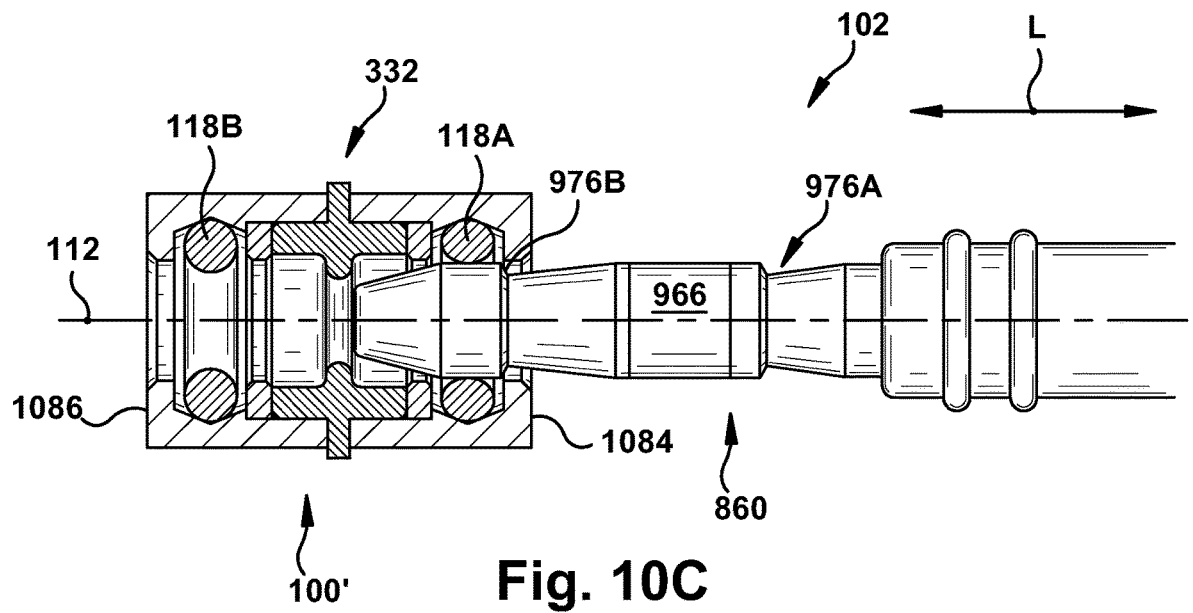

As shown in FIG. 10C, the tapered portion of the pin shaft 966 has passed beyond the first canted coil spring 118A under the insertion force. When the inner spring circumference 120A is sized for an "interference fit" with the connector pin 860, a lateral component of the insertion force is present and is pushing the first inner spring circumference outward from the bore axis 112. The first canted coil spring 118A may resist this lateral "spreading" through the "compression" or "deflection" forces developed within the first canted coil spring. Optionally, this resistance developed in the first canted coil spring 118A will help assist with laterally centering the pin shaft 966 within the bore axis 112.

Because the first canted coil spring 118A is configured with a first inner spring circumference 120A which is smaller than the (at least local) maximum shaft circumference 974, the connector pin 860 slides longitudinally past the first canted coil spring in contact therewith. Alternately, when the first canted coil spring 118A is configured with a first inner spring circumference 120A which is larger than the (at least local) maximum shaft circumference 974, it is contemplated that the connector pin 860 could move longitudinally past the first canted coil spring without contact there between. This latter situation may occur, for example, if the first and second housing shells 104A and 104B, and/or components thereof, are differently dimensioned to achieve desired electrical and/or mechanical connections between the connector pin 860 and the multi-shell socket 100' in a nonuniform manner.

Figure 10D:
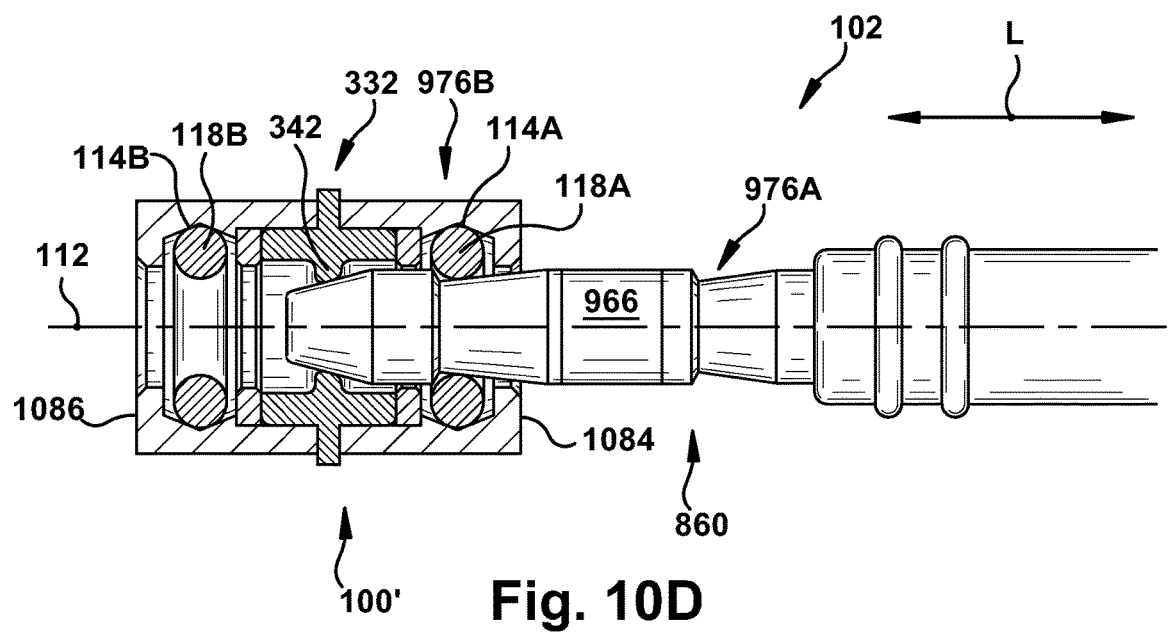

Once the connector pin 860 has been inserted sufficiently into the bore axis 112, the first canted coil spring 118A is allowed to at least partially rebound from the laterally-oriented component of the insertion force, as shown in FIG. 10D, through alignment of the first canted coil spring and the second v-groove 976B in the same longitudinal location relative to each other—that is, both of these structures are located in substantially the same location along the bore axis 112. The relatively sudden decrease in circumference of the pin shaft 966 caused by the obtuse angle α of the second v-groove 976B allows the first canted coil spring 118A to "snap" into the v-groove. In other words, at least a portion of the first canted coil spring 118A laterally enters the second v-groove 976B under influence of the spring force developed within the first canted coil spring to bias the inner spring circumference 120A into its resting state. A maintenance force, therefore, develops laterally between the first canted coil spring 118A and the connector pin 860 at the second v-groove 976B. Optionally, the "snapping" action of the asymmetrical-force connector system 102 provides the user with a tactile and/or aural indication that the first stage of engagement between the connector pin 860 and the multi-shell socket 100' has occurred.

In addition, for many use environments of the present invention, the asymmetrical-force connector system 102 will complete an electrical circuit by virtue of the first canted coil spring 118A coming into electrical contact with at least a portion of the second v-groove 976B. In other words, the first canted coil spring 118A may create an electrical circuit/connection by coming into concurrent electrically conductive contact with both the second v-groove 976B and the first spring-receiving cavity 114A. In this manner, electrical signals can be passed between the connector pin 860 and the socket 100.

Also optionally, when the components of the asymmetrical-force connector system 102 have reached the arrangement shown in FIG. 10D, the inner intermediate circumference 342 could exert a force laterally against the pin shaft 966 when the connector pin 860 is located in a maintenance position, with a canted coil spring of the socket 100 "snapped" into a corresponding v-groove of the connector pin. Particularly if the intermediate member 332 is made of a relatively resilient material, the inner intermediate circumference 342 could thus perform a "sealing" function against the pin shaft 966 to prevent fluid (e.g., blood) from flowing between the first and second canted coil springs 118A and 118B, and perhaps shorting out the electrical connections desired by the user of the asymmetrical-force connector system 102.

Figure 10E:
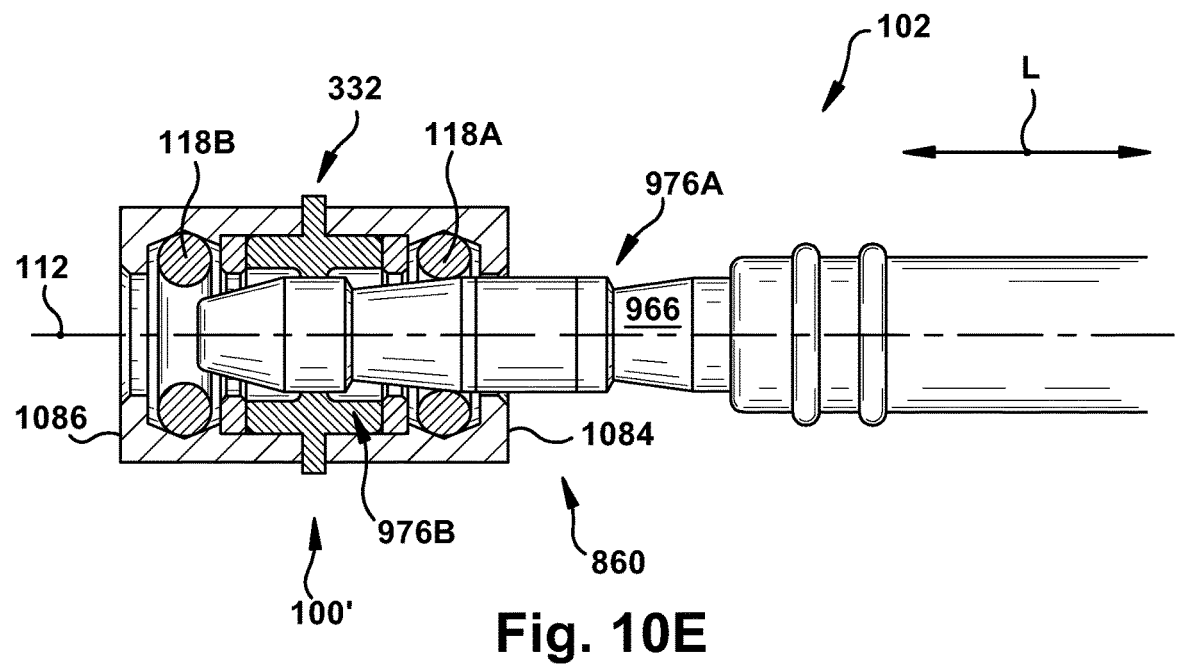

As the connector pin 860 continues to move in the insertion direction (toward the left, in the orientation of FIGS. 10A-10I), the pin shaft 966 enters further into the shaft bore 110. As shown in FIG. 10E, the laterally oriented maintenance force existing between the first canted coil spring 118A and the second v-groove 976B in the FIG. 10D view has been overcome via force exerted to move the connector pin 860 in the insertion direction. While the asymmetrical-force connector system 102 continues along the insertion sequence of FIGS. 10A-10I, the relatively gradual slope of the proximal groove face 980A (a product of the acute angle β) pushes laterally outward from the bore axis 112 against the first inner spring circumference 120A to overcome the maintenance force and thus "ramp" the first canted coil spring 118A out of the second v-groove 976B and into the arrangement of FIG. 10F.

Figure 10F:
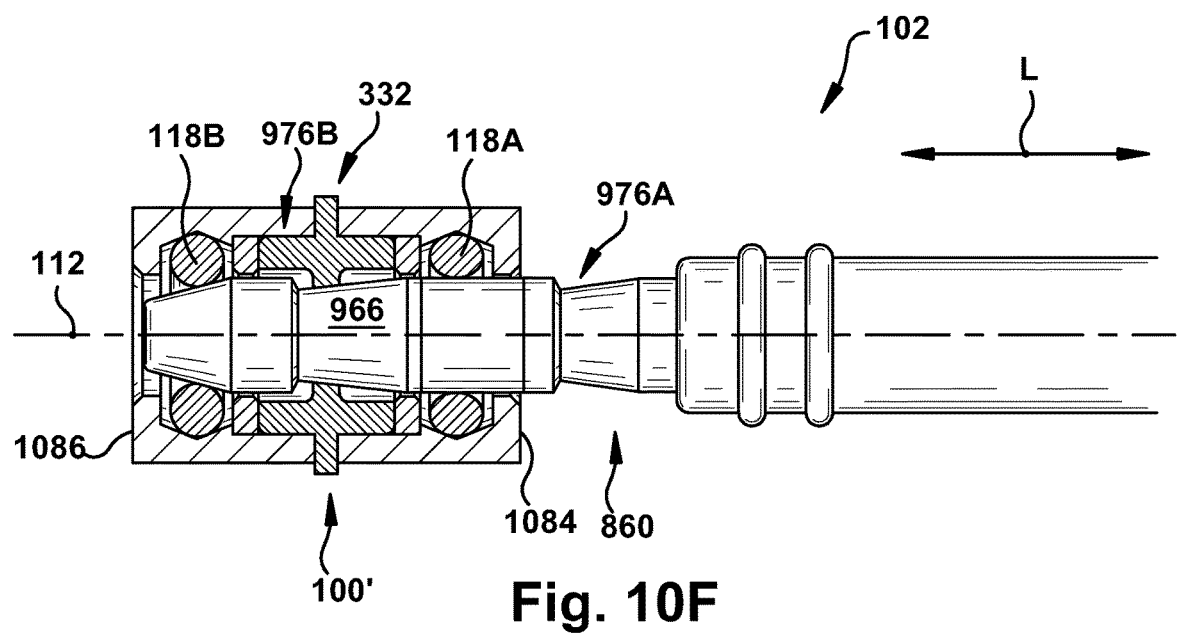

In FIG. 10F, the first inner spring circumference 120A of the first canted coil spring 118A is once again held "open" by a non-v-grooved portion of the pin shaft 966—here, a portion of the pin shaft having the maximum shaft circumference 974 is located longitudinally aligned (i.e., within the same cross-section taken perpendicular to the bore axis 112) with the first canted coil spring 118A. Also in FIG. 10F, the distal shaft end 970 has passed through the second canted coil spring 118B and the tapered area of the pin shaft 966 is pushing the second inner spring circumference 120B laterally outward from the bore axis 112 in much the same way that the pin shaft dilated the first inner spring circumference 120A in FIG. 10B.

Figure 10G:
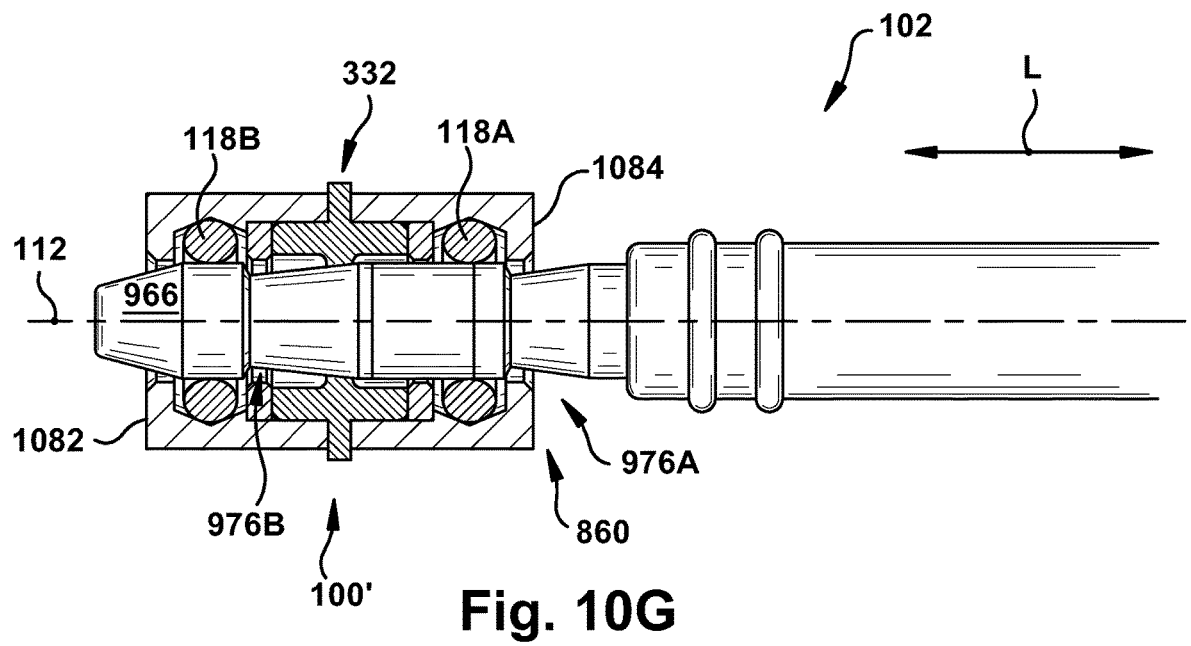

Proceeding in the insertion sequence from FIG. 10F to FIG. 10G, both the first and second canted coil springs 118A and 118B are being held "open" by a laterally-oriented component of the insertion force which is driving the connector pin 860 to slide past the first and second canted coil springs. As the push-type insertion motion continues, under the influence of at least the longitudinal component of the insertion force, the components of the asymmetrical-force connector system 102 enter the relative positioning/arrangement shown in FIG. 10H.

Figure 10H:
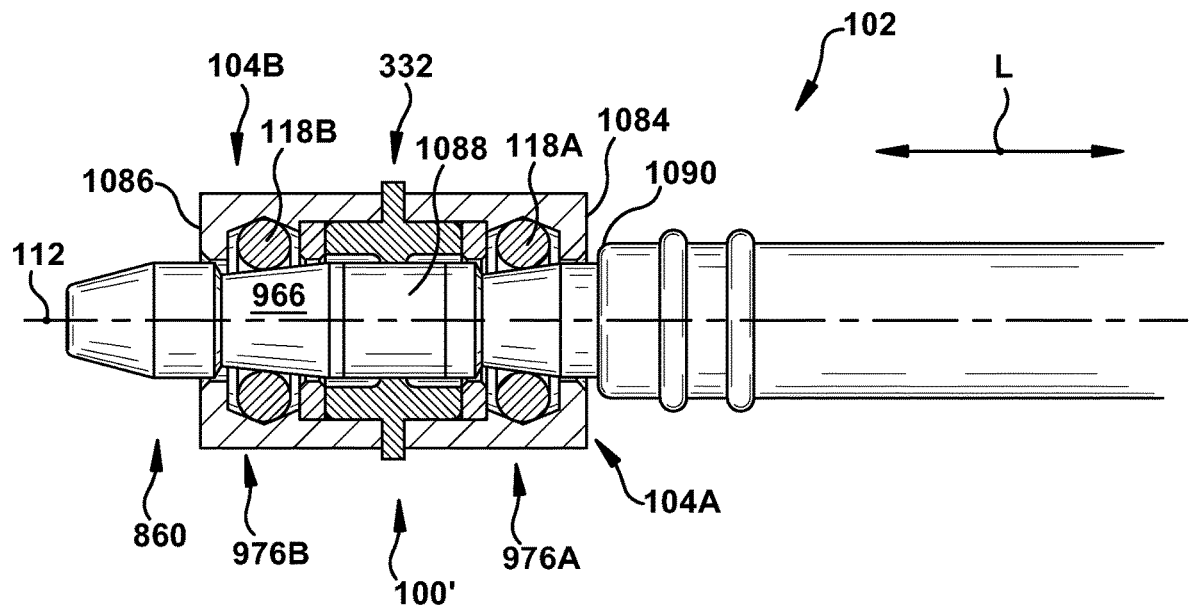

In FIG. 10H, the first and second canted coil springs 118A and 118B have both "snapped" into the first and second v-grooves 976A and 976B, respectively, similar to the "snapping" action described above with reference to the initial groove/spring engagement shown in FIG. 10D. In the arrangement of FIG. 10H, the first and second canted coil springs 118A and 118B have both been subjected to a relatively abrupt reduction in the circumference of the pin shaft 966, from the (at least locally) maximum shaft circumference 974 to the (at least locally) minimum shaft circumference 978 at the apex of the first and second v-grooves 976A and 976B, due to the obtuse angles α of these two v-grooves. This "snapping" action could provide the user with a tactile and/or aural indication that the connector pin 860 has become fully engaged with the multi-shell socket 100'. The connector pin 860 and multi-shell socket 100' may remain in the FIG. 10H arrangement (A.K.A., a "maintenance position") to achieve a relatively long-term indwelling mechanical and/or electrical connection via the asymmetrical-force connector system 102. Stated differently, the connector pin 860 is located in a "maintenance position" within the shaft bore 110 when at least a portion of the connector pin is located longitudinally between the front and rear socket faces 1084 and 1086 (which could be front or rear housing faces, as discussed above), with at least a portion of at least one of the first and/or second canted coil springs 118A and 118B laterally extending into at least one of the first and second v-grooves 976A and 976B, the canted coil spring extending "beyond" (i.e., further laterally inward from) the maximum shaft circumference 974. Optionally, the first and/or second v-groove 976A and 976B may be held in mechanical and/or electrical contact with a respected first and/or second canted coil spring 118A and 118B via a maintenance force when the connector pin 860 is located in the maintenance position within the shaft bore 110.

Also optionally, and as shown in the Figures, the connector pin 860 could include an insulator band 1088. Particularly when the first and second canted coil springs 118A and 118B are used to create an electrical connection between the first and second v-grooves 976A and 976B and the respective spring-receiving cavities 114A and 114B, the insulator band 1088 could be configured to contact, or even "seal" against via lateral force, the inner intermediate circumference 342 of the sealing disc 340 of the intermediate member 332. As shown in FIG. 10H, this "sealing" function between the insulator band 1088 and the intermediate member 332 may help to electrically and/or physically isolate the first and second housing shells 104A and 104B from each other.

In addition, some component of the asymmetrical-force connector system 102 or a related structure could be used to provide a "stop" function and avoid unwanted over-insertion of the connector pin 860 into the shaft bore 110. For example, as the connector pin 860 is inserted into the multi-shell socket 100', a shoulder 1090 (here, an increased-diameter structure that is too large to fit into the shaft bore 110) or other "stop" feature could be provided. When present, the shoulder 1090 or other "stop" feature could have a predetermined longitudinal positioning with respect to at least one of the first and second v-grooves 976A and 976B to physically interfere with insertion of the connector pin 860 into the multi-shell socket 100'. Using the depicted shoulder 1090 as an example, the shoulder could impinge upon the front socket face 1084 to halt longitudinal movement of the connector pin 860 in the insertion direction.

Figure 10I:
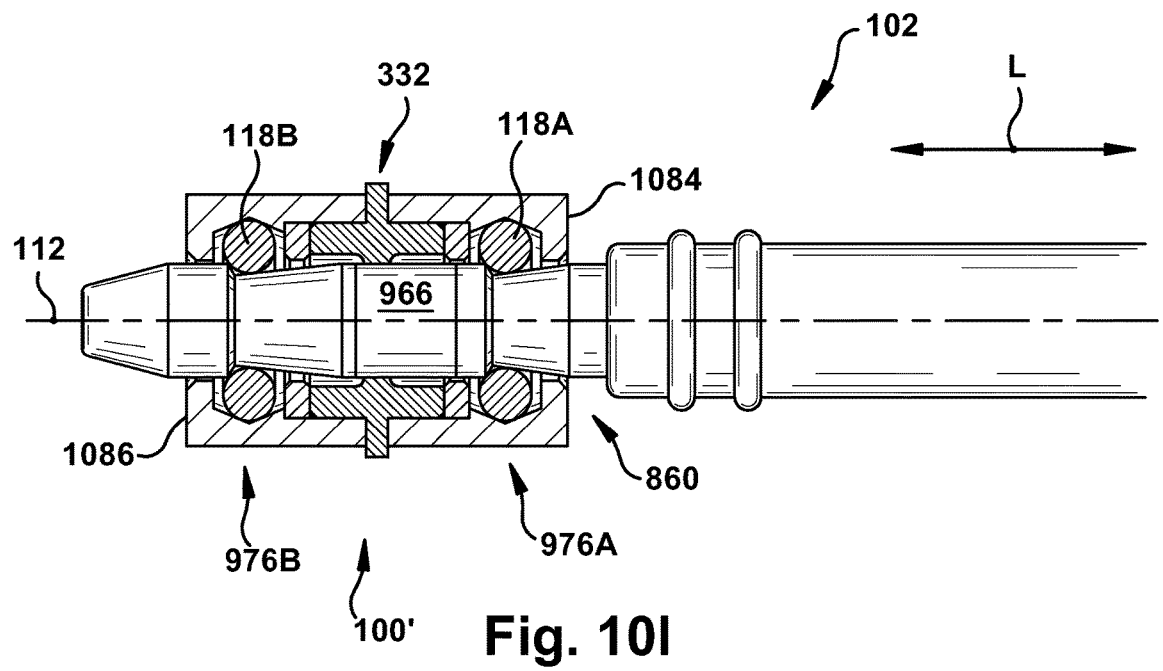

From the maintenance position in FIG. 10H, the connector pin 860 may be at least partially retracted from the shaft bore 110 under the influence of a retraction force, oppositely directed from the insertion force (i.e., exerted from the left toward the right side of FIGS. 10A-10I), into the retraction position of FIG. 10I. As the connector pin 860 is pulled in the retraction direction, the first and second canted coil springs 118A and 118B come into contact with the distal groove faces 982A and 982B. Because of the relatively large obtuse angles α of the first and second v-grooves 976A and 976B, the first and second canted coil springs 118A and 118B must be relatively suddenly compressed laterally outward to permit passage there through of the pin shaft 966. The retraction force must therefore be sufficient to overcome the maintenance force and "jump" the first and second inner spring circumferences 120A and 120B laterally outward to permit passage of the maximum shaft circumference 974 there through as the connector pin 860 is retracted or withdrawn from the multi-shell socket 100'.

As previously mentioned, an insertion force, which may be primarily longitudinally-oriented, is exerted upon the connector pin 860 to advance the first and second distal groove faces 982A and 982B of the first and second v-grooves 976A and 976B past the first and second canted coil springs 118A and 118B. This total insertion force may include needed force to advance the second proximal groove face 984B past the first canted coil spring 118A, as shown in FIG. 10E, as well. A maintenance force, which may be primarily laterally-oriented, may then be developed between the first and second v-grooves 976A and 976B and the first and second canted coil springs 118A and 118B to hold the connector pin 860 and the multi-shell socket 100' in the maintenance position. A retraction force, which may be primarily longitudinally-oriented, is then exerted upon the connector pin 860 to retract the first and second proximal groove faces 984A and 984B of the first and second v-grooves 976A and 976B past the first and second canted coil springs 118A and 118B. This total retraction force may include needed force to retract the second distal groove face 982B past the first canted coil spring 118A, as well.

In many use environments of the present invention, an "easy-in, tough-out" relationship between the connector pin 860 and the multi-shell socket 100' may be desired. For example, and as discussed in the background section of this application, a user may wish to connect implanted medical devices using a relatively low insertion force, but the indwelling asymmetrical-force connector system 102 may desirably have a relatively high retraction force to resist pullout or disconnection during a maintenance phase of ordinary use of the medical devices. This asymmetry may be achieved in some embodiments of the present invention by coordinating orientation of one or more of the canted coil springs 118 of the system. For example, and with reference to the previously discussed spring configurations #1 through #4, both the first and second canted coil springs 118A and 118B in a completed multi-shell socket 100 may be oriented in the same direction within their respective spring-receiving cavities 114A and 114B, as viewed by an outside observer (e.g., in FIGS. 10A-10I), even though other components of the first and second housing shells 104A and 104B may be mirror images of each other. The described asymmetry may be increased through design of the v-grooves 976, and particularly the obtuse and acute angles $\alpha$ and $\beta$. The asymmetrical-force connector system 102 of the present invention can be configured to require a retraction force that is substantially greater than the insertion force. In other words, while the acute angle $\beta$ helps support electrical and/or mechanical contact between the connector pin 860 and the multi-shell socket 100' when these components are in the maintenance position, the obtuse angle $\alpha$ contributes to a relatively steep distal groove face 982 which affects the retraction force needed to remove the connector pin from the multi-shell socket.

The term "substantially greater" is used herein to indicate that the retraction force is at least measurably larger than the insertion force—for example, for some embodiments of the present invention, the (larger) retraction force could be in the range of 1.50-10.00 Newtons, as opposed to a (smaller) insertion force in the range of 0.25-5.00 Newtons. The retraction and insertion forces for a particular use environment of the present invention could be "tuned" or controlled by the choice of obtuse, acute, and/or included angles $\alpha$, $\beta$, and $\gamma$ for the v-groove(s) 976 and/or by choice of handedness, installation orientation, and/or canting direction for at least one canted coil spring 118. Optionally, the retraction and insertion forces may bear a predictable relationship to each other (e.g., proportional), which could arise from particular configurations of the first and second canted coil springs 118A and 118B.

The dimensions and configurations of the first and second canted coil springs 118A and 118B, as well as other components of the asymmetrical-force connector system 102, may also be provided by one of ordinary skill in the art to achieve desired insertion and retraction resistances in a single assembly. For example, for certain use environments of the present invention, 32-36 rotations (coils) of the canted coil springs 118A and 118B may provide desired insertion and retraction resistances. The inner spring circumferences 120A and 120B may be, for example, in the range of 0.034-0.040 inches. As another example, and particularly in medical device use environments, the socket 100 itself could have fairly small dimensions, such as a lateral outer diameter in the range of 0.104-0.112 inches and a longitudinal height in the range of 0.165-0.170 inches. It has been found that, particularly for diminutively-sized sockets 100, currently commercially available canted coil springs 118 having the same nominal physical properties may vary widely in actual dimensions and spring forces. Accordingly, the dimensions and interactions of the components of the asymmetrical-force connector system 102 which collectively provide the different retraction and insertion forces may be designed and/or adjusted to account for the variances in commercially available canted coil springs 118.

From the arrangement shown in FIG. 10I, the retraction force may be maintained to reverse the sequence of operation shown in FIGS. 10A-10H and remove the connector pin 860 from the multi-shell socket 100'. The asymmetrical-force connector system 102 then is in a disassembled state. Depending upon the use environment of the present invention, the asymmetrical-force connector system 102 may then be reconnected, possibly with differently configured structures (e.g., a connector pin 860 electrically connected to a different device component) through repetition of the insertion sequence of FIGS. 10A-10I.

Figure 11:
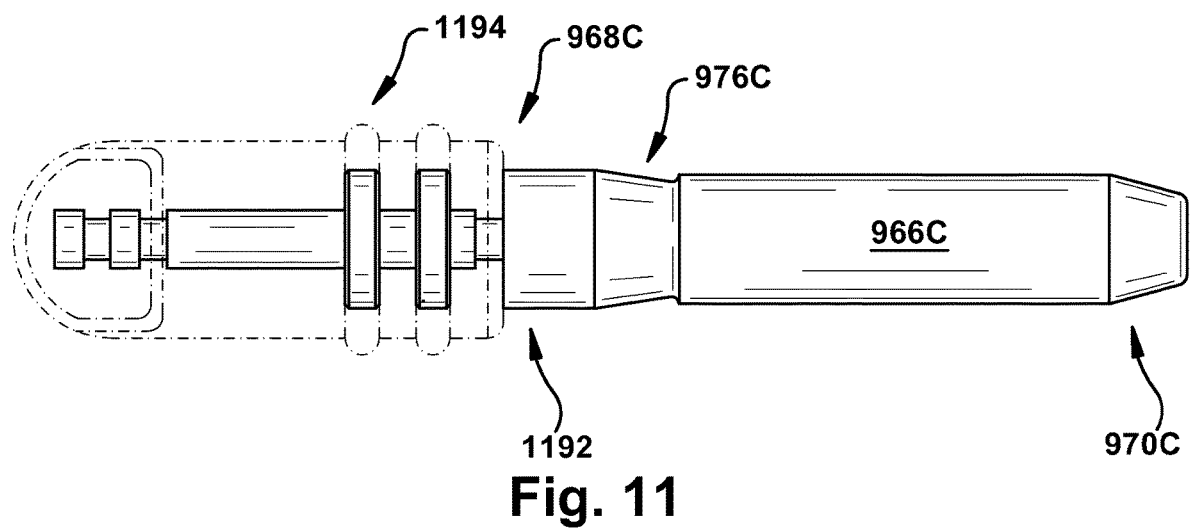
FIG. 11 is a partial side view of an alternate component for use with the embodiment of FIG. 8.
Figure 12:
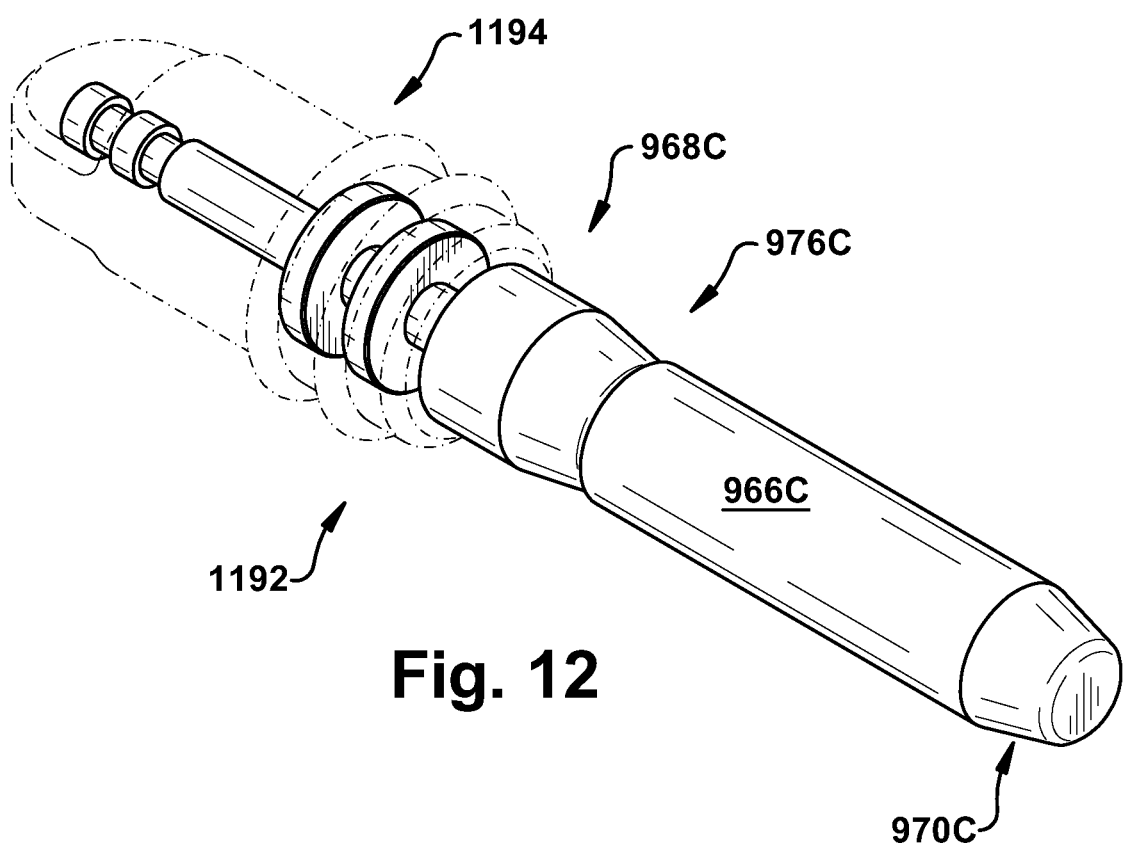
FIG. 12 is a perspective view of the alternate component of FIG. 11.

Optionally, and with reference to FIGS. 11-12, a port-plug 1192 could be provided to fill an unused shaft bore 110 (e.g., of the socket manifold 748) to prevent entry of undesired substances (e.g., blood) from an ambient environment. The port-plug 1192 and associated structures are similar to the connector pin 860 and therefore, structures of the port-plug that are the same as or similar to those described with reference to the connector pin have the same reference numbers with the addition of the suffix "C". Description of common elements and operation similar to those related to the connector pin 860 will not be repeated with respect to the port-plug 1192.

The port-plug 1192 includes a shaft 966C which is sized to extend into/through the shaft bore 110 of both the first and second housing shells 104A and 104B of the multi-shell socket 100', but only a single v-groove 976C is provided on the port-plug. A stub end 1194 is located on the proximal shaft end 968C. The port-plug 1192 is inserted into the shaft bore 110 substantially similarly to the insertion of the connector pin 860 shown in FIGS. 10A-10I and described above. However, since the port-plug only has a single v-groove 976C, the second inner spring circumference 120B of the second canted coil spring 118B will remain laterally forced/"stretched" outward from the bore axis 112 when the first inner spring circumference 120A of the first canted coil spring 118A has "snapped" into the v-groove 976C of the port-plug. Optionally, the shaft 966C or other components of the port-plug 1192 may include insulator bands or other insulating or conducting features (not shown) to achieve long-term electrical and/or mechanical isolations or connections when the port-plug is used to block an unused socket 100 of an asymmetrical-force connector system 102. In other words, the port-plug 1192 could act as a "blind" connector pin 860 and cap off a proximal end of the shaft bore 110 to provide a plug function to the asymmetrical-force connector system 102 when the port-plug 1192 type connector pin 860 is located in a maintenance position within the shaft bore.

The purpose of the single v-groove 976C configuration of the port-plug 1192 is at least in part to avoid wear on the first canted coil spring 118A of a multi-shell socket 100' such as that of FIGS. 10A-10I. The steeper the obtuse angle $\alpha$ of a particular v-groove 976, the higher retraction force will be needed to remove a connector pin 860 or a port-plug 1192 from a socket 100 and therefore the more stress will be seen by a canted coil spring 118 interacting with that v-groove.

"Deflection cycling" of the canted coil springs 118 (i.e., the compression/release cycle caused by interaction with a v-groove 976) during connector pin 860 insertion and retraction is a significant contributor to wear or even failure of the canted coil springs. The diminutive canted coil springs 118 used in miniature use applications such as medical device connections may fail after fewer, possibly far fewer, than one hundred of these deflection cycles. The first canted coil spring 118A of a multi-shell socket 100' will see twice as many deflection cycles in use than the second canted coil spring 118B of the same socket, because the first canted coil spring interacts with both the first and second v-grooves 976A and 976B during insertion/retraction of the connector pin 860, while the second canted coil spring 118B only interacts with the second v-groove 976B. However, mere compression (i.e., being pressed outward by the shaft) does not have as much of a deleterious effect on the canted coil springs 118 as does deflection cycling.

Moreover, the port-plug 1192 has a relatively short stub end 1194 that is not subject to the pullout forces that may be developed in a connecting wire or device component extending a significant distance away from a connecting pin 860 in maintenance position in a socket 100. Accordingly, the port-plug 1192 does not need to be held as firmly within the shaft bore 110 as would an "active" (i.e., non-plug-type) connector pin 860. Since a reduced magnitude retraction force is acceptable for a port-plug 1192 and reduced deflection cycling may be desirable to support later usage of the port-plug-blocked socket 100 with an active connector pin 860, a port-plug having a single v-groove 976C, longitudinally aligned with the first canted coil spring 118A in the maintenance position, may be an acceptable compromise to save wear on the first and second canted coil springs 118A and 118B during the lifetime of the socket 100.

While the above description uses an electrical connection between first and second components 858 and 864 as an example, the interconnect device 746, or subassemblies/elements thereof, could also or instead be used to make a mechanical connection between the first and second components, even if no electrical connection exists at the time of connection formation or at any other time. The first and second components 858 and 864, along with any additional components (not shown) which are also electrically connected using the interconnect device 746, may be components of any type of apparatus/device, such as, but not limited to, an implanted medical device (not shown).

It should also be understood that the number and type of canted coil springs 118 in the multi-shell socket 100 may provide a multiplier value to the quantitative insertion and retraction forces. For example, with all other factors being equal, providing a second canted coil spring 118B arrangement which is substantially similar to a first canted coil spring 118A which is already present would effectively double the forces developed during operation of the asymmetrical-force connector system 102. Similarly, providing a third canted coil spring arrangement (not shown) would effectively triple those forces. One of ordinary skill in the art will be able to specify types and numbers of canted coil springs 118 to achieve desired forces for a particular use environment of the present invention.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the asymmetrical force connector system 102 and/or interconnect device 746 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials such as, but not limited to, stainless steel, titanium, platinum, nickel-cobalt alloy MP35N, Nitinol, Polyether ether ketone, epoxies, urethanes, metals, polymers, ceramics, and the like; however, the chosen material(s) should be biocompatible for many applications of the present invention. While the above depiction presumes that the connector pin 860 is removed from the socket 100 by reversal of the insertion motion (in other words, by movement in the retraction direction) to remove the connector pin from the front of the socket, it is also contemplated that, in some use environments, the connector pin 860 could pass entirely longitudinally through the shaft bore 110 and exit through the rear of the socket. Though certain components described herein are shown as having specific geometric shapes, all structures of the present invention may have any suitable shapes, sizes, configurations, relative relationships, cross-sectional areas, or any other physical characteristics as desirable for a particular application of the present invention. The above description references "maximum" and "minimum" dimensions, but these could be local maximums/minimums—it is contemplated that some other areas of the described structures, spaced apart from the interfacing structures of the asymmetrical-force connector system 102, could have dimensions larger than the aforementioned "maximum" or smaller than the aforementioned "minimum". Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. More than two housing shells 104, linked by multiple intermediate members 332 or in any other way, may be connected together into a longitudinally-oriented "stack" of any suitable length. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:
1. An asymmetrical-force connector system, comprising:
  a socket, including:
    a housing shell, having oppositely disposed front and rear housing faces and a longitudinally-oriented shaft bore extending longitudinally through the housing shell and linking the front and rear housing faces, the shaft bore defining a bore axis,
    a spring-receiving cavity being coaxial with the bore axis and extending laterally around an entirety of the shaft bore, the spring-receiving cavity having an inner circumference that is open to the shaft bore, and a toroidal canted coil spring located at least partially within the spring-receiving cavity, the toroidal canted coil spring having a laterally-oriented inner spring circumference coaxial with the bore axis and extending laterally around an entirety of the shaft bore; and a connector pin, configured for selective sliding insertion into the shaft bore longitudinally from the front housing face, the connector pin including:

an elongate shaft having proximal and distal shaft ends and defining a pin axis, the shaft having a laterally-oriented maximum shaft circumference that is larger than the inner spring circumference, and a v-groove extending laterally inward from the maximum shaft circumference toward the pin axis, the v-groove being located longitudinally between the proximal and distal shaft ends and extending circumferentially around the entirety of the shaft to define a minimum shaft circumference as the apex of an included angle, as viewed perpendicular to the pin axis, the v-groove having a proximal groove face extending laterally and proximally outward from the minimum shaft circumference of the shaft at an acute angle with respect to the pin axis and a distal groove face extending laterally and distally outward from the minimum shaft circumference of the shaft at an obtuse angle with respect to the pin axis;

wherein the connector pin is located in a maintenance position within the shaft bore when at least a portion of the connector pin is located longitudinally between the front and rear housing faces with at least a portion of the toroidal canted coil spring laterally extending into the v-groove beyond the maximum shaft circumference;

wherein the housing shell is a first housing shell having oppositely disposed front and rear first housing faces and a first shaft bore, the system including a second housing shell having oppositely disposed front and second rear housing faces and a longitudinally-oriented second shaft bore extending longitudinally through the second housing shell and linking the front and second rear housing faces, the second shaft bore being located collinearly with the first shaft bore, and the second front housing face is located longitudinally interposed between the rear first housing face and the second rear housing face, a second spring-receiving cavity is coaxial with the bore axis and extending laterally around an entirety of the second shaft bore, the second spring-receiving cavity having a second inner spring circumference that is open to the second shaft bore, and a second toroidal canted coil spring is located at least partially within the second spring-receiving cavity, the second toroidal canted coil spring having a laterally-oriented second inner spring circumference coaxial with the bore axis and extending laterally around an entirety of the second shaft bore;

wherein an intermediate member is interposed longitudinally between the second front housing face and the rear first housing face, the intermediate member and first and second housings cooperatively defining the shaft bore therethrough, the intermediate member having a laterally-oriented inner intermediate circumference that is longitudinally coaxial with both of the first and second inner spring circumferences;

wherein the inner intermediate circumference is laterally smaller than both of the first and second inner spring circumferences, the intermediate member is at least partially made of a resilient material, and the intermediate member provides a sealing function longitudinally between the first and second toroidal canted coil springs and laterally against the shaft when the connector pin is located in the maintenance position.

2. The asymmetrical-force connector system of claim 1, wherein the v-groove is a first v-groove and the connector pin includes a second v-groove extending laterally inward from the maximum shaft circumference toward the pin axis, the second v-groove being located longitudinally between the first v-groove and the distal shaft end and extending circumferentially around the entirety of the shaft to define a second minimum shaft circumference as the apex of an included angle, as viewed perpendicular to the pin axis, the second v-groove having a proximal second groove face extending laterally and proximally outward from the second minimum shaft circumference of the shaft at an acute angle with respect to the pin axis and a distal second groove face extending laterally and distally outward from the second minimum shaft circumference of the shaft at an obtuse angle with respect to the pin axis, and wherein the connector pin is located in a maintenance position within the shaft bore when at least a portion of the connector pin is located longitudinally between the front and rear housing faces with at least a portion of the first toroidal canted coil spring laterally extending into the first v-groove beyond the maximum shaft circumference and at least a portion of the second toroidal canted coil spring laterally extending into the second v-groove beyond the maximum shaft circumference.

3. The asymmetrical-force connector system of claim 1, wherein the distal shaft end has a terminal diameter that is smaller than the maximum shaft circumference.

4. The asymmetrical-force connector system of claim 1, wherein the proximal shaft end is in electrical communication with a component of an implanted electrical medical device.

5. The asymmetrical-force connector system of claim 1, wherein the v-groove is in electrical contact with the toroidal canted coil spring when the connector pin is located in a maintenance position within the shaft bore.

6. The asymmetrical-force connector system of claim 1, wherein a proximal end of the shaft bore is capped off to provide a plug function to the system when the connector pin is located in a maintenance position within the shaft bore.

7. The asymmetrical-force connector system of claim 1, wherein the v-groove has an included angle in the range of 90-148 degrees.

8. The asymmetrical-force connector system of claim 1, wherein the slidable insertion of the connector pin through the shaft bore through the front housing face longitudinally toward the rear housing face into the maintenance position develops an insertion force between the v-groove and the toroidal canted coil spring, the slidable retraction of the connector pin through the shaft bore through the rear housing face longitudinally away from the rear housing face from the maintenance position develops a retraction force of between the v-groove and the toroidal canted coil spring, and the retraction force is substantially greater than the insertion force.

9. An interconnect device for selectively electrically connecting first and second components to each other using the asymmetrical-force connector system of claim 1, wherein the socket is in electrical contact with the first component and the connector pin is in electrical contact with the second component, and wherein the connector pin is inserted into the socket to place the first and second components into electrical contact with each other via an electrically-connective interface between the socket and the connector pin.

10. The interconnect device of claim 9, wherein a plurality of sockets are in direct electrical contact with the first component, at least one connector pin is in direct electrical contact with the second component, and wherein at least one connector pin is inserted into a corresponding one of the sockets to place the first and second components into electrical contact with each other via an electrically-connective interface between the socket and the connector pin.

11. The interconnect device of claim 10, wherein the plurality of sockets comprise a socket manifold.

12. A method of use of an asymmetrical-force connector system, the method comprising the steps of:
   providing the asymmetrical-force connector system of claim 1
   inserting at least a portion of the connector pin longitudinally into the shaft bore;
   passing at least a portion of the connector pin through the inner spring circumference in a longitudinally-oriented insertion direction;
   compressing the toroidal canted coil spring laterally outward from the bore axis by exerting an insertion force against the toroidal canted coil spring with the portion of the connector pin passing therethrough;
   allowing the toroidal canted coil spring to at least partially rebound from the insertion force by aligning the toroidal canted coil spring and the v-groove in the same longitudinal location relative to each other, such that at least a portion of the toroidal canted coil spring laterally enters the v-groove and a maintenance force develops laterally between the toroidal canted coil spring and the connector pin at the v-groove;
   overcoming the maintenance force with a retraction force to pass at least a portion of the connector pin through the inner spring circumference in a longitudinally-oriented retraction direction, longitudinally opposite the insertion direction;
   compressing the toroidal canted coil spring laterally outward from the bore axis by exerting the retraction force against the toroidal canted coil spring with the portion of the connector pin passing therethrough; and
   removing the connector pin from the socket;
   wherein the retraction force, to overcome the maintenance force and allow the connector pin to move in the retraction direction is substantially greater than the insertion force to move the connector pin in the insertion direction due to the relative configurations of the v-groove and the toroidal canted coil spring.

13. The method of claim 12, including the steps of:
   placing the connector pin in electrical communication with a first component of an implanted electrical medical device;
   placing the socket in electrical communication with a second component of the implanted electrical medical device; and
   inserting the connector pin at least partially into the shaft bore to place the first and second components of the implanted electrical medical device in electrical communication with each other.

\* \* \* \* \*

UNITED STATES PATENT AND TRADEMARK OFFICE
CERTIFICATE OF CORRECTION

PATENT NO. : 10,634,181 B2
APPLICATION NO. : 15/747265
DATED : April 28, 2020
INVENTOR(S) : Frederick W. Montague and Brian Smith Page 1 of 1

It is certified that error appears in the above-identified patent and that said Letters Patent is hereby corrected as shown below:

In the Specification

Immediately after the TITLE please insert the following Paragraph:
--FEDERAL FUNDING NOTICE
This invention was made with government support under the grants EB001740 and NS041809 awarded by the National Institutes of Health. The government has certain rights in the invention.--

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*